(12) United States Patent
Popov

(10) Patent No.: US 11,871,820 B2
(45) Date of Patent: Jan. 16, 2024

(54) DEVICE, SYSTEM, AND METHOD FOR PROMOTING PATIENT COMPLIANCE WITH A PRESCRIBED LOWER EXTREMITY PARTIAL WEIGHT-BEARING REHABILITATION PROGRAM

(71) Applicant: Illia Popov, Dnipro (UA)

(72) Inventor: Illia Popov, Dnipro (UA)

( * ) Notice: Subject to any disclaimer, the term of this patent is extended or adjusted under 35 U.S.C. 154(b) by 96 days.

(21) Appl. No.: 17/522,751

(22) Filed: Nov. 9, 2021

(65) Prior Publication Data
US 2023/0143646 A1   May 11, 2023

(51) Int. Cl.
| | | |
|---|---|---|
| *A45B 3/08* | (2006.01) | |
| *A45B 9/04* | (2006.01) | |
| *A61H 3/02* | (2006.01) | |
| *G06F 3/14* | (2006.01) | |
| *G01L 5/16* | (2020.01) | |

(Continued)

(52) U.S. Cl.
CPC ............. *A45B 3/08* (2013.01); *A45B 9/04* (2013.01); *A61H 3/0288* (2013.01); *G01L 5/16* (2013.01); *G06F 3/14* (2013.01); *G16H 20/30* (2018.01); *A61H 2201/5023* (2013.01); *A61H 2201/5061* (2013.01); *A61H 2201/5097* (2013.01); *G06F 3/0482* (2013.01)

(58) Field of Classification Search
CPC ...... G09B 19/16; G09B 5/00; G06Q 10/0639; G06Q 10/06398; A45B 3/08; A45B 9/04; A61H 3/0288; G01L 5/16; G06F 3/14; G16H 20/30

See application file for complete search history.

(56) References Cited

U.S. PATENT DOCUMENTS

| | | |
|---|---|---|
| 5,511,571 A | 4/1996 | Adrezin et al. |
| 7,610,802 B2 | 11/2009 | Clar et al. |

(Continued)

FOREIGN PATENT DOCUMENTS

| | | |
|---|---|---|
| CN | 103340735 B | 11/2015 |
| CN | 111956226 | 11/2020 |

(Continued)

OTHER PUBLICATIONS

Rajesh et al., Design and Implementation of Intelligent Crutches for Medical Applications, Apr. 23, 2019 (Year: 2019).*

(Continued)

*Primary Examiner* — Eddy Saint-Vil

(57) ABSTRACT

In one aspect, an electronic device for promoting proper use of a walking aid during lower extremity injury rehabilitation comprises at least one load sensor configured to measure a load on the walking aid. A memory stores rehabilitation program data defining at least one time interval of a rehabilitation period and, for each time interval, a target load for the walking aid during the time interval. A currently operative time interval of the at least one time interval of the rehabilitation period is identified. Data is received, from the load sensor(s), indicative of a dynamic load on the walking aid during a patient step. Based upon the received data, a peak load upon the walking aid during the patient step is determined. A user notification indicating that the peak load is non-compliant with the target load for the walking aid for the currently operative time interval is provided.

16 Claims, 23 Drawing Sheets

(51) Int. Cl.
*G16H 20/30* (2018.01)
*G06F 3/0482* (2013.01)

(56) References Cited

U.S. PATENT DOCUMENTS

| | | | |
|---|---|---|---|
| 8,758,272 | B2 | 6/2014 | Kubiak et al. |
| 8,915,132 | B1 | 12/2014 | Ward |
| 9,360,343 | B2 | 6/2016 | Stevens et al. |
| 9,826,806 | B2 | 11/2017 | Challa |
| 10,722,144 | B2 | 7/2020 | Nakao |
| 10,733,866 | B2 | 8/2020 | Rabinowitz et al. |
| 10,799,154 | B2 | 10/2020 | Sarkar et al. |
| 10,849,395 | B2 | 12/2020 | Aubin et al. |
| 11,207,003 | B2 | 12/2021 | Fukushi et al. |
| 2006/0273913 | A1* | 12/2006 | Clar ............... A61B 5/1036 361/136 |
| 2013/0041590 | A1* | 2/2013 | Burich ............ G16H 40/63 702/19 |
| 2017/0224573 | A1 | 8/2017 | Challa |
| 2018/0296426 | A1 | 10/2018 | Kappel |
| 2019/0231631 | A1 | 8/2019 | Campilii |
| 2019/0240103 | A1 | 8/2019 | Hepler et al. |
| 2022/0117828 | A1* | 4/2022 | Aluru ............ A61H 3/0277 |

FOREIGN PATENT DOCUMENTS

| | | |
|---|---|---|
| DE | 2704520 A1 | 8/1978 |
| DE | 10214745 A1 | 2/2003 |
| DE | 102009057424 B4 | 9/2012 |
| DE | 102013001192 A1 | 7/2014 |
| EP | 1519701 B1 | 12/2009 |
| EP | 2729096 A1 | 5/2014 |
| EP | 2 688 472 B1 | 4/2016 |
| EP | 3838143 A1 | 6/2021 |
| ES | 1249804 U | 10/2020 |
| FR | 3088533 A1 | 5/2020 |
| UA | 144685 U | 3/2021 |
| WO | 200136051 | 5/2001 |
| WO | 2013134330 | 9/2013 |
| WO | 2021234208 A1 | 11/2021 |
| WO | 2022013678 A1 | 1/2022 |
| WO | 2022074540 | 4/2022 |
| WO | 2022079564 A1 | 4/2022 |

OTHER PUBLICATIONS

Tamburella, et al., Load Auditory Feedback Boosts Crutch Usage in Subjects With Central Nervous System Lesions: A Pilot Study, Jul. 6, 2021 (Year: 2021).*

International Search Report and Written Opinion for International PCT patent application No. PCT/IB2022/060731 dated Jan. 31, 2023.

Megalingam Rajesh Kannan et al., "Design and Implementation of Intelligent Crutches for Medical Applications," 2019 International Conference on Communication and Signal Processing (ICCSP), IEEE, Apr. 4, 2019, pp. 926-929.

Narvaez, Marien et al., Gait Patterns Monitoring Using Instrumented Forearm Crutches, International Conference on Computers Helping People with Special Needs (ICCHP 2020), LNCS 12377, pp. 402-410, Sep. 4, 2020, Department of Automatic Control (ESAII), Polytechnic University of Catalonia, Barcelona, Spain, https://doi.org/10.1007/978-3-030-58805-2_48.

Sesar, Inigo et al., Instrumented Crutch Tip for Monitoring Force and Crutch Pitch Angle, Multidisciplinary Digital Publishing Institute (MDPI) Sensors, 2019, 19, 2944, Published Jul. 4, 2019, https://www.mdpi.com/1424-8220/19/13/2944.

Sardini, Emilio et al., Wireless Instrumented Crutches for Force and Movement Measurements for Gait Monitoring, IEEE Transactions on Instrumentation and Measurement, 2015, vol. 64, Issue 12.

Chen, Yongqi Felix et al., Smart Crutches: Towards Instrumented Crutches for Rehabilitation and Exoskeletons-Assisted Walking, 2018 7th IEEE International Conference on Biomedical Robotics and Biomechatronics (Biorob) Enschede, The Netherlands, Aug. 26-29, 2018.

Merrett, Geoff V. et al., Augmenting forearm crutches with wireless sensors for lower limb rehabilitation, Measurement Science and Technology, vol. 21 (12): 10—Dec. 1, 2010.

Seylan, Caglar, Estimation of ground reaction forces using forearm crutches instrumented with pressure sensors and accelerometers, Thesis—Middle East Technical University, Feb. 2016.

Popov, Illia, Ukrainian transcript of YouTube Video ComeBack Mobility^ "Стисло про проект розумних милиць", , URL https://www.youtube.com/watch?v=FrODhffiBsl, Posted Aug. 14, 2020, with English language translation.

Popov, Illia, transcript of YouTube Video ComeBack Mobility^, URL https://www.youtube.com/watch?v=5PTSJC-ZYO8 , Posted Sep. 2, 2020.

* cited by examiner

144

| 1/18/21 | 1/19/21 | 1/20/21 | 1/21/21 | 1/22/21 | 1/23/21 | 1/24/21 |
|---|---|---|---|---|---|---|
| 200 lbs. | 200 lbs. | 200 lbs. | 200 lbs. | 200 lbs. | 200 lbs. | 200 lbs. |

144-1, 144-2, 144-3, 144-4, 144-5, 144-6, 144-7

| 1/25/21 | 1/26/21 | 1/27/21 | 1/28/21 | 1/29/21 | 1/30/21 | 1/31/21 |
|---|---|---|---|---|---|---|
| 200 lbs. | 200 lbs. | 200 lbs. | 200 lbs. | 200 lbs. | 200 lbs. | 200 lbs. |

144-8, 144-9, 144-10, 144-11, 144-12, 144-13, 144-14

| 2/1/21 | 2/2/21 | 2/3/21 | 2/4/21 | 2/5/21 | 2/6/21 | 2/7/21 |
|---|---|---|---|---|---|---|
| 140 lbs. | 140 lbs. | 140 lbs. | 140 lbs. | 140 lbs. | 140 lbs. | 140 lbs. |

144-15, 144-16, 144-17, 144-18, 144-19, 144-20, 144-21

| 2/8/21 | 2/9/21 | 2/10/21 | 2/11/21 | 2/12/21 | 2/13/21 | 2/14/21 |
|---|---|---|---|---|---|---|
| 140 lbs. | 140 lbs. | 140 lbs. | 140 lbs. | 140 lbs. | 140 lbs. | 140 lbs. |

144-22, 144-23, 144-24, 144-25, 144-26, 144-27, 144-28

| 2/15/21 | 2/16/21 | 2/17/21 | 2/18/21 | 2/19/21 | 2/20/21 | 2/21/21 |
|---|---|---|---|---|---|---|
| 140 lbs. | 134 lbs. | 128 lbs. | 122 lbs. | 115 lbs. | 109 lbs. | 103 lbs. |

144-29, 144-30, 144-31, 144-32, 144-33, 144-34, 144-35

| 2/22/21 | 2/23/21 | 2/24/21 | 2/25/21 | 2/26/21 | 2/27/21 | 2/28/21 |
|---|---|---|---|---|---|---|
| 97 lbs. | 91 lbs. | 85 lbs. | 78 lbs. | 72 lbs. | 66 lbs. | 60 lbs. |

DEVICE, SYSTEM, AND METHOD FOR PROMOTING PATIENT COMPLIANCE WITH A PRESCRIBED LOWER EXTREMITY PARTIAL WEIGHT-BEARING REHABILITATION PROGRAM

TECHNICAL FIELD

The present disclosure relates to device, system, and method for promoting patient compliance with a prescribed lower extremity partial weight-bearing rehabilitation program.

BACKGROUND

A lower extremity injury, such as trauma to or surgery upon a toe, foot, ankle, calf, knee, thigh, or hip, may require rehabilitation to promote proper healing. Rehabilitation typically involves walking with the assistance of a walking aid that bears at least part of the weight of the user, such as a crutch, a pair of crutches, a cane, a pair of canes, or a walker.

Rehabilitation is typically performed according to a rehabilitation program prescribed by a doctor or other medical professional. The rehabilitation program may span multiple weeks and may have one or more phases. During each phase, a different partial weight-bearing (load) target may be prescribed for the injured lower extremity. The target load may be expressed as a fraction of a peak load normally placed upon the lower extremity while walking, which is 100% of the person's weight.

A medical professional may customize the parameters of a rehabilitation program, such as its duration, number of phases, and the target load for each phase. The parameters may be specific to the type of lower extremity injury that has been suffered.

In one example, a rehabilitation program for a patient with a heel fracture may have only one phase spanning four weeks, specifying a target load of 30% of the patient's weight on the injured leg throughout the four-week period.

In another example, a rehabilitation program for a patient who has recently undergone hip replacement surgery may have three phases spanning seven weeks, as follows:

Phase 1: three weeks of 0% load on the injured hip; then
Phase 2: two weeks of a 30% load on the injured hip; then
Phase 3: two weeks of a progressively increasing load on the injured hip, starting at 30% load and increasing steadily to 70%.

Historically, patients have had difficulty complying with the target loads of lower extremity rehabilitation programs. The reason is that commonly used rehabilitation techniques do not provide patients with suitable tools for accurately judging a degree of load being placed upon a lower extremity as the patient walks.

For example, a common approach for training a patient to apply a partial weighting target to an injured lower extremity involves the use of a scale, e.g., a common bathroom scale. The patient may be asked to step onto the scale using the injured leg while suspending the other leg and partially supporting himself or herself on a pair of crutches whose tips are on the floor. The patient may then be asked to lean more heavily or less heavily on the crutches until a target load on the injured leg is achieved. The target weight reading on the scale will depend on the patient's weight. For example, for a patient weighing 200 lbs. to achieve 40% weighting on the injured leg, the scale should read 80 pounds.

Such training may be repeated several times to encourage the patient to remember what the target percentage weighting on the injured leg feels like. The patient may then be asked to simply do his or her best to replicate that same feeling during day-to-day use of the crutches, to comply with the target load during rehabilitation.

Yet, limitations in human perception can undermine attempts by even the most well-intentioned patients to comply with weight-bearing targets by feel. For example, sensation in an injured lower extremity may change over time for various reasons. One reason may be that perceived pain levels drop as the injury heals. Another reason may be that sensation in the injured extremity may change over the course of a day, e.g., as a patient becomes fatigued. Such changes in sensation may alter the patient's perception of the amount of weight being applied to the injured lower extremity. This altered perception may cause the patient to unknowingly apply an improper load, be it too low or too high, on the injured lower extremity. Improper loading may disadvantageously prolong recovery times or may risk re-injuring the lower extremity.

Patient compliance with partial weight-bearing targets may be even more difficult to achieve when a rehabilitation program specifies a target load that changes over time, such as in the hip replacement example above. Just when a patient has become accustomed to the feel of one target load, he or she may be asked to comply with a new, different target load with which the patient may not be readily familiar in terms of feel.

Even if a device were available that could dynamically measure a weight applied to an injured lower extremity in relation to a target weight, such a device would be impractical if periodic reprogramming were required to accommodate a changing weight-bearing target load over the course of a rehabilitation program.

SUMMARY

In one aspect, there is provided an electronic device for promoting proper use of a walking aid during patient rehabilitation from a lower extremity injury, the device comprising: at least one load sensor configured to measure a load on the walking aid; a memory that, during device operation, stores rehabilitation program data defining: at least one time interval of a rehabilitation period; and for each of the at least one time interval, a target load for the walking aid during the time interval; a processor, communicatively coupled to the memory and to the at least one load sensor, operable to: identify a currently operative time interval of the at least one time interval of the rehabilitation period; receive, from the at least one load sensor, data indicative of a dynamic load on the walking aid during a patient step; determine, based upon the received data, a peak load upon the walking aid during the patient step; and provide a user notification indicating that the peak load upon the walking aid during the patient step is non-compliant with the target load for the walking aid for the currently operative time interval.

In another aspect, there is provided A system for promoting proper use of a walking aid during patient rehabilitation from a lower extremity injury, the system comprising: an electronic device associated with the walking aid, the electronic device comprising: at least one load sensor configured to measure a load on the walking aid; and a processor communicatively coupled to the at least one load sensor; a computing device comprising a processor and memory storing instructions that, when executed, cause the computing device to: receive rehabilitation program parameter data originating from a medical professional, the rehabilitation program parameter data including, for each of a plurality of time intervals spanning a rehabilitation period, a target relative load for an injured lower extremity during the time interval, the target relative load being relative to a patient body weight; receive an indication of the patient body weight; based on the rehabilitation program parameter data and the patient body weight, calculate, for each of the plurality of time intervals spanning the rehabilitation period, a target absolute load for the walking aid during the time interval; and output rehabilitation program data comprising a schedule for use by the electronic device associated with the walking aid, the schedule specifying: the plurality of time intervals spanning the rehabilitation period; and for each of the plurality of time intervals spanning the rehabilitation period, a target absolute load for the walking aid during the time interval, wherein the processor of the electronic device is operable to automatically adjust, according to the schedule, a currently operative target absolute load on the walking aid by, periodically during the rehabilitation period: based on a current date, identifying one of the time intervals of the schedule as currently operative; using the at least one load sensor, determining a peak load on the walking aid during a patient step taken during the currently operative time interval; and providing a user notification indicating that the peak load upon the walking aid during the patient step is non-compliant with the target absolute load on the walking aid during the currently operative time interval.

In yet another aspect, there is provided a method of promoting proper use of a walking aid during patient rehabilitation from a lower extremity injury, the method comprising: receiving rehabilitation program parameter data originating from a medical professional, the rehabilitation program parameter data including, for each of a plurality of time intervals spanning a rehabilitation period, a target relative load on an injured lower extremity during the time interval, the target relative load being relative to a patient body weight; receiving an indication of the patient body weight; based on the rehabilitation program parameter data and the patient body weight, calculating, for each of the plurality of time intervals spanning the rehabilitation period, a target absolute load on the walking aid during the time interval; and generating rehabilitation program data comprising a schedule specifying: the plurality of time intervals spanning the rehabilitation period; and for each of the plurality of time intervals spanning the rehabilitation period, a target absolute load on the walking aid during the time interval, and at an electronic device associated with the walking aid, the electronic device having at least one load sensor operable to measure a dynamic load on the walking aid, automatically adjusting, according to the schedule, a currently operative target absolute load on the walking aid by, periodically during the rehabilitation period: based on a current date, identifying one of the time intervals of the schedule as currently operative; using the at least one load sensor, determining a peak load on the walking aid during a patient step taken during the currently operative time interval; and providing a user notification indicating that the peak load upon the walking aid during the patient step is non-compliant with the target absolute load on the walking aid during the currently operative time interval.

BRIEF DESCRIPTION OF THE DRAWINGS

In the figures which illustrate example embodiments,

FIG. 10 depicts a data structure used at a primary smart crutch tip electronic device of FIG. 1;

DETAILED DESCRIPTION

In this document, the term "exemplary" should be understood to mean "an example of" and not necessarily to mean that the example is preferable or optimal in some way. Terms such as "upper", "lower", and "above" may be used to describe some embodiments in this description but should not be understood to necessarily connote an orientation of the embodiments during manufacture or use.

Figure 1:
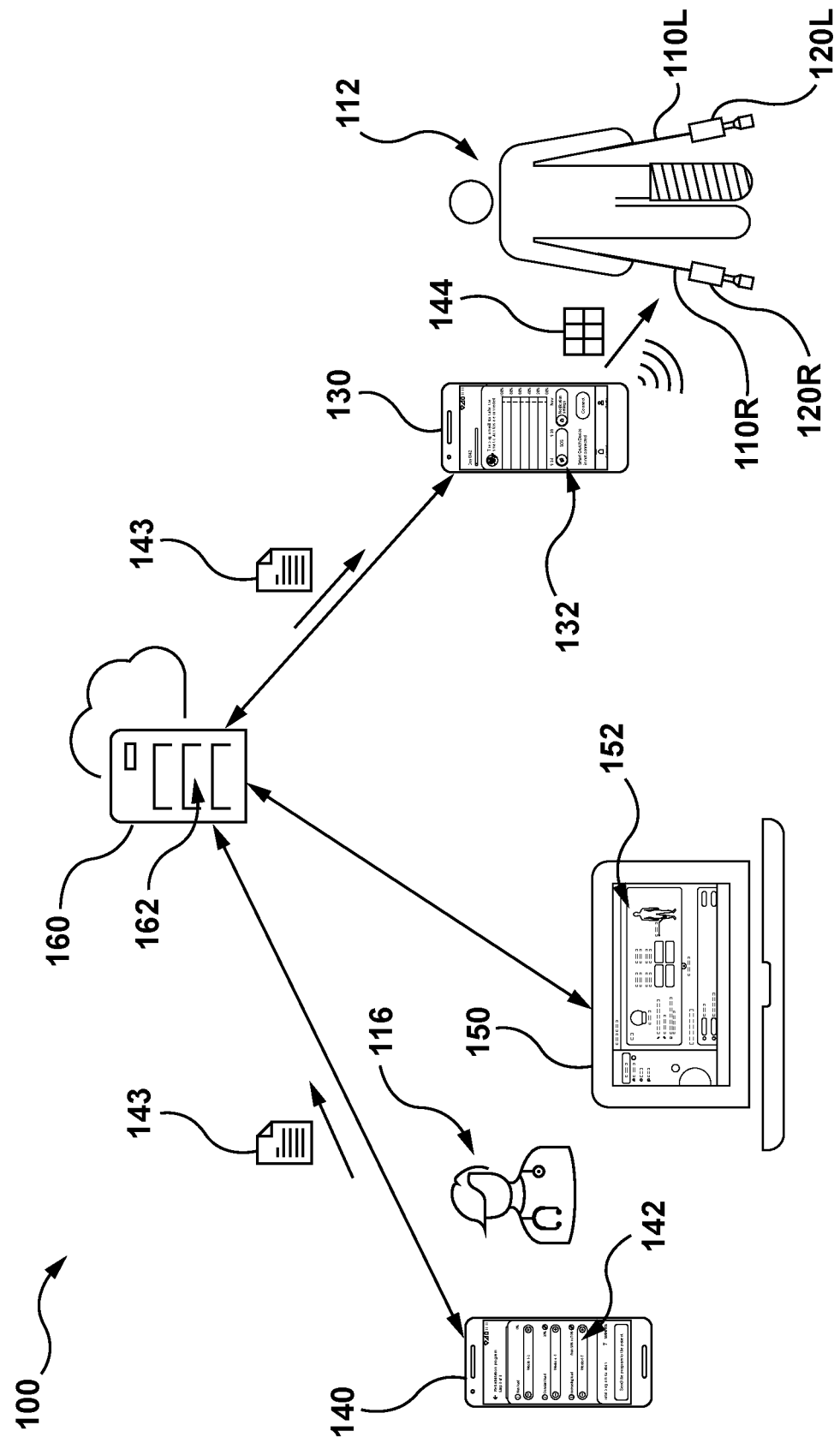
FIG. 1 is a schematic diagram of an example system for promoting proper use of a during lower extremity rehabilitation.

FIG. 1 is a schematic diagram of an exemplary system 100 for promoting proper use of a walking aid 110 by a patient 112 during lower extremity rehabilitation. In this example, the walking aid 110 is a pair of crutches 110R, 110L (generically or collectively crutch(es) 110), and the lower extremity is an injured left leg. Alternative embodiments of the system may be used with other types of walking aids and for other types of lower extremity injuries.

The depicted example system 100 has various components, including: two smart crutch tip devices 120L and 120R (generically or collectively smart crutch tip device(s) 120), which have been installed onto crutches 110L and 110R (generically or collectively crutch(es) 110) respectively in a manner that will be described; a mobile device 130, used by the patient 112, executing a mobile patient software application ("app") 132; a mobile device 140, used by a doctor 116, executing a mobile doctor app 142; a computer 150, also used by the doctor 116, executing a web-based doctor app 152; and a cloud-based server 160 executing a backend server application 162.

Each of the smart crutch tips 120 is an electronic device that is attachable to a respective one of crutches 110 to dynamically measure the load placed on the crutch 110 as it is being used by the patient 112. The smart crutch tips 120R, 120L are designed to intercommunicate wirelessly in order to amalgamate dynamic load information from the two crutches at one of the smart crutch tips 120R, referred to as the "primary" smart crutch tip. This is done to permit a collective (total) load on the pair of crutches 110 to be computed in real time for each step taken using the crutches, as will be described below.

In overview, the smart crutch tips 120 are designed to promote patient compliance with a lower extremity rehabilitation program that has been prepared specifically for the patient 112 by the doctor 116. The smart crutch tips 120 do this by receiving and utilizing patient-specific rehabilitation program data 144 based on rehabilitation program parameters originating from the doctor 116. The data 144 specifies a duration of the rehabilitation program (the "rehabilitation period") during which the patient should use the crutches 110, e.g., expressed as a number of days, and specifies (indirectly) a weight-bearing target on the injured lower extremity for each day of the rehabilitation program.

Upon receipt of the rehabilitation program data 144, the smart crutch tips 120 configure themselves to monitor for patient compliance with the daily weight-bearing target as the crutches are used. More specifically, the smart crutch tips 120 use the current date and time to determine which day of the rehabilitation program is currently operative. The smart crutch tips 120 then indirectly determine the weight being placed on the injured lower extremity during each step by measuring how much of the patient's weight is being carried by the crutches 110. That load is compared to the target load for the crutches for the current day.

Based on the results of the comparison, feedback is provided to the patient 112, in real time, in the form of one or more configurable user notifications, e.g., visual indicators, auditory indicators, or voice indicators. The user notification(s) indicate(s) whether the weight placed on the injured lower extremity is too high or too low. Absence of a user notification may indicate compliance with the target load, which may include being within a range of tolerance of the target. Usage data may also be continuously or periodically wirelessly communicated to the patient mobile device 130 and relayed to the cloud-based server 160 for near real-time access by the doctor 116 in monitoring for patient compliance with the rehabilitation program from a remote location.

By way of the foregoing mechanisms, the smart crutch tips 120 are operable to automatically adjust the weight-bearing targets for the injured lower extremity (i.e., a currently operative target load on the walking aid) over time in accordance with the rehabilitation program schedule originally prescribed by the doctor 116 for the patient 112. Moreover, the smart crutch tips 120 can automatically adapt themselves to monitor for compliance with dynamically changeable weight bearing targets during the rehabilitation period.

It should be appreciated that the smart crutch tips 120 do not directly measure the amount of weight placed on the injured lower extremity. Rather, the smart crutch tips 120 compute a peak weight on the pair of crutches 110 at a point in the patient's gait at which the patient's weight will simultaneously be on the crutches and on the injured lower extremity. The smart crutch tips 120 operate on the presumption that, at that moment of the patient's gait, whatever portion of the patient's weight is not on the crutches will be on the injured lower extremity. This is perhaps best understood with reference to FIG. 2.

Figure 2:
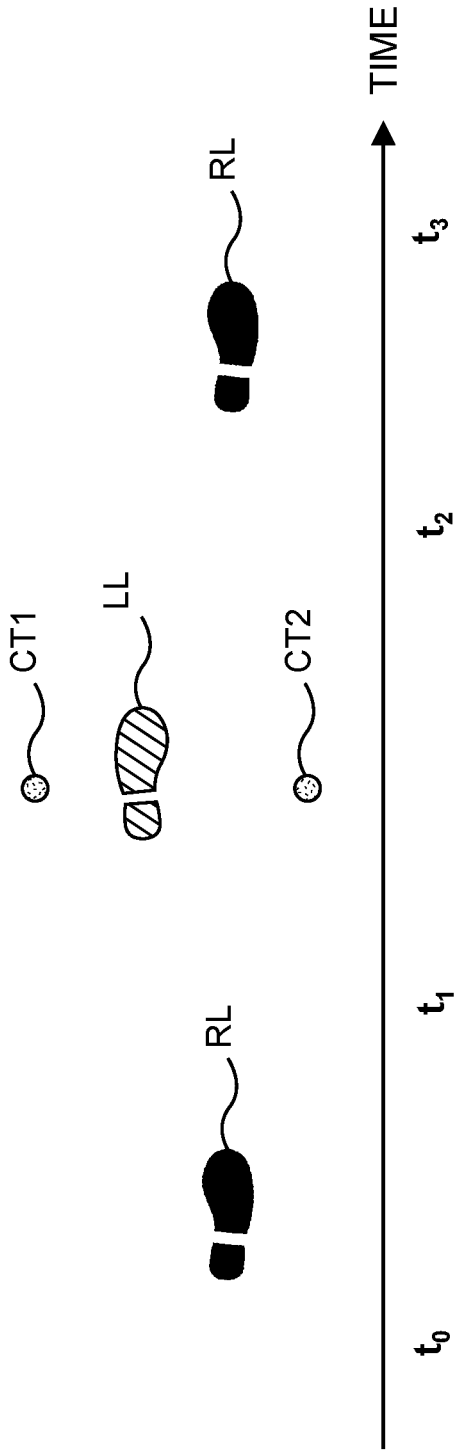
FIG. 2 is a schematic diagram depicting the gait of a patient having an injured left leg walking with the assistance a pair of crutches.

FIG. 2 schematically depicts the gait of a patient having an injured left lower extremity (e.g., left leg) and an uninjured right leg, walking with the assistance a pair of crutches. Time is representing on the horizontal axis. Three steps of the patient's gait are depicted in FIG. 2.

In a first step (step 1) taken between time t0 and time t1, the patient places 100% of his or her weight on the uninjured right leg RL. During step 1, neither the tips of the crutches nor the injured leg is on the ground. Rather, the crutch tips are being swung forwardly in anticipation of step 2, and the injured leg is suspended.

In a second step (step 2) taken between time t1 and t2, the patient plants two crutch tips on the ground at points CT1 and CT2 respectively. At approximately the same time as the crutch tips are planted, the patient steps lightly on the injured left leg LL while using the crutches to steady himself or herself. At this time, the uninjured leg RL is swinging forwardly in anticipation of step 3, i.e., is not on the ground. As a result, part of the patient's weight will be on the injured leg, and the remainder of the patient's weight will be on the crutches at this time. It is at this moment that the weight on the injured leg can be deduced (indirectly measured) by measuring the weight on the pair of crutches and subtracting it from the patient's body weight. This is the principle by which the smart crutch tips 120 operate to indirectly measure the weight placed on the injured leg.

The third patient step (step 3), taken between time t2 and t3, is a repetition of step 1. The cycle is thereafter repeated with step 4 (not depicted) being a repetition of step 2, and so on. As will be appreciated, the measuring of the body weight on the crutches is only performed during alternate steps—in this example, step 2, step 4, and so forth.

An example embodiment of a smart crutch tip 120 is illustrated in FIGS. 3, 4, 5, and 6 in perspective view, elevation view, cross-sectional view (taken along line 5-5 of FIG. 4), and exploded view, respectively. FIG. 7 is a schematic diagram depicting a simplified representation of a lower portion of the smart crutch tip 120 in cross-section when attached to a crutch leg.

As illustrated in FIGS. 3-6, the smart crutch tip 120 has a housing 202 that houses and protects structural and electronic components of the smart crutch tip 120. In the depicted embodiment, the housing has two halves to facilitate device assembly. The first half is an upper housing portion 204, which is substantially cylindrical in the present embodiment. The second half is a lower housing portion 206, which is generally funnel-shaped in the present embodiment. The housing 202 may have different shapes and/or different components in alternative embodiments.

Figure 4:
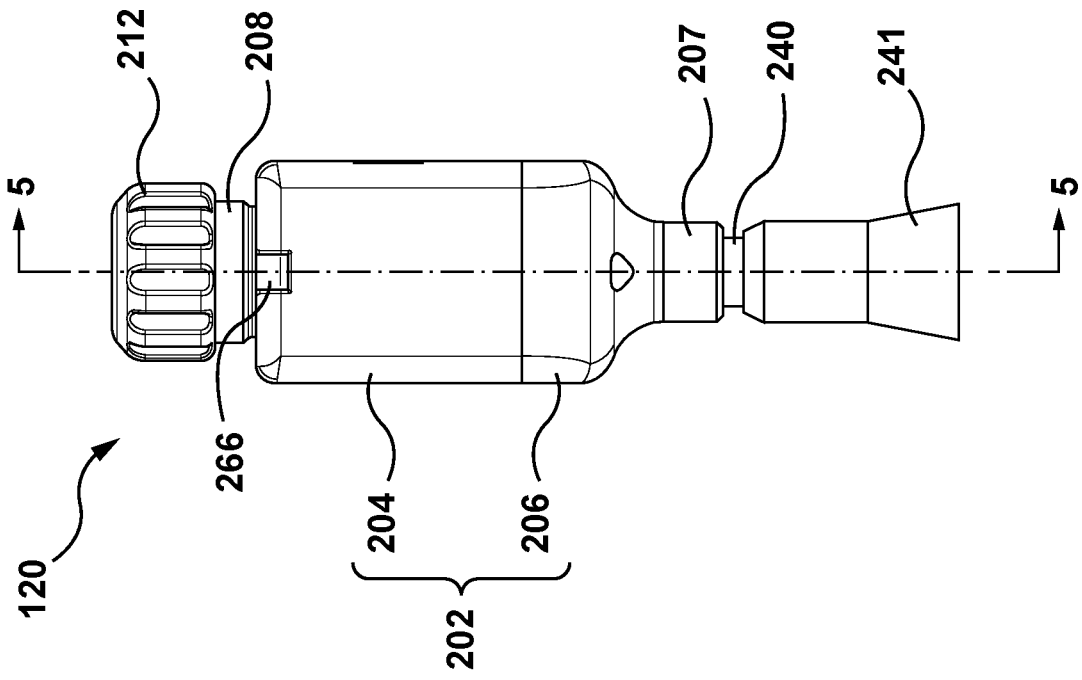
FIG. 4 is an elevation view of the smart crutch tip electronic device of FIG. 3.
Figure 3:
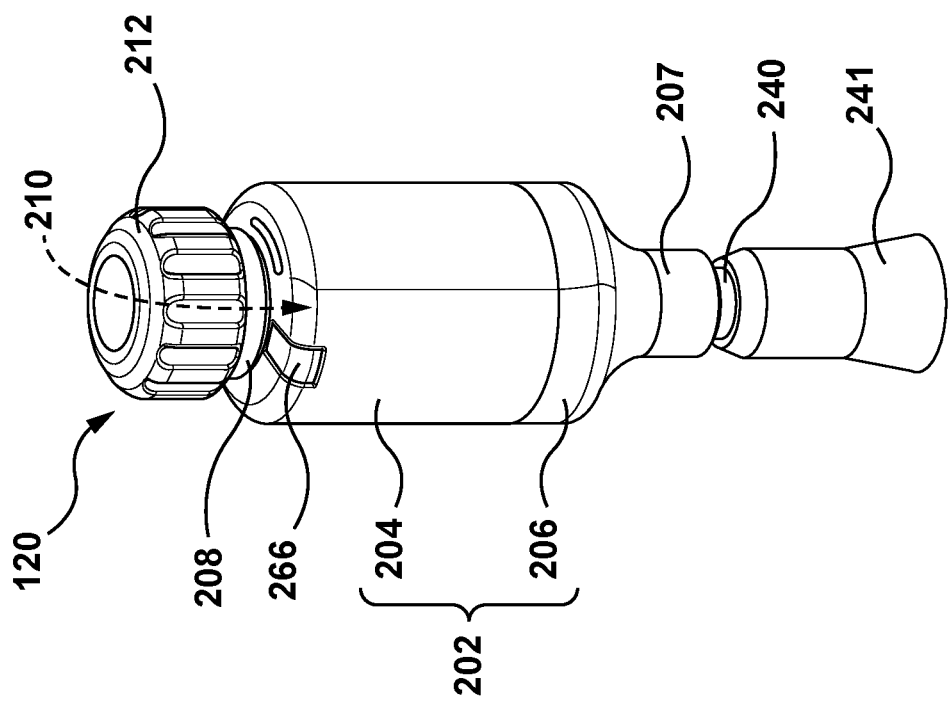
FIG. 3 is a perspective view of one of the smart crutch tip electronic devices of FIG. 1.

The structural components of the smart crutch tip 120 include a body 208, only partly visible in FIGS. 3 and 4. The body 208 may be considered as the primary structural component or frame of the smart crutch tip 120. It may be made from a rigid, strong, lightweight material, such as aluminum or suitable plastic for example.

Figure 5:
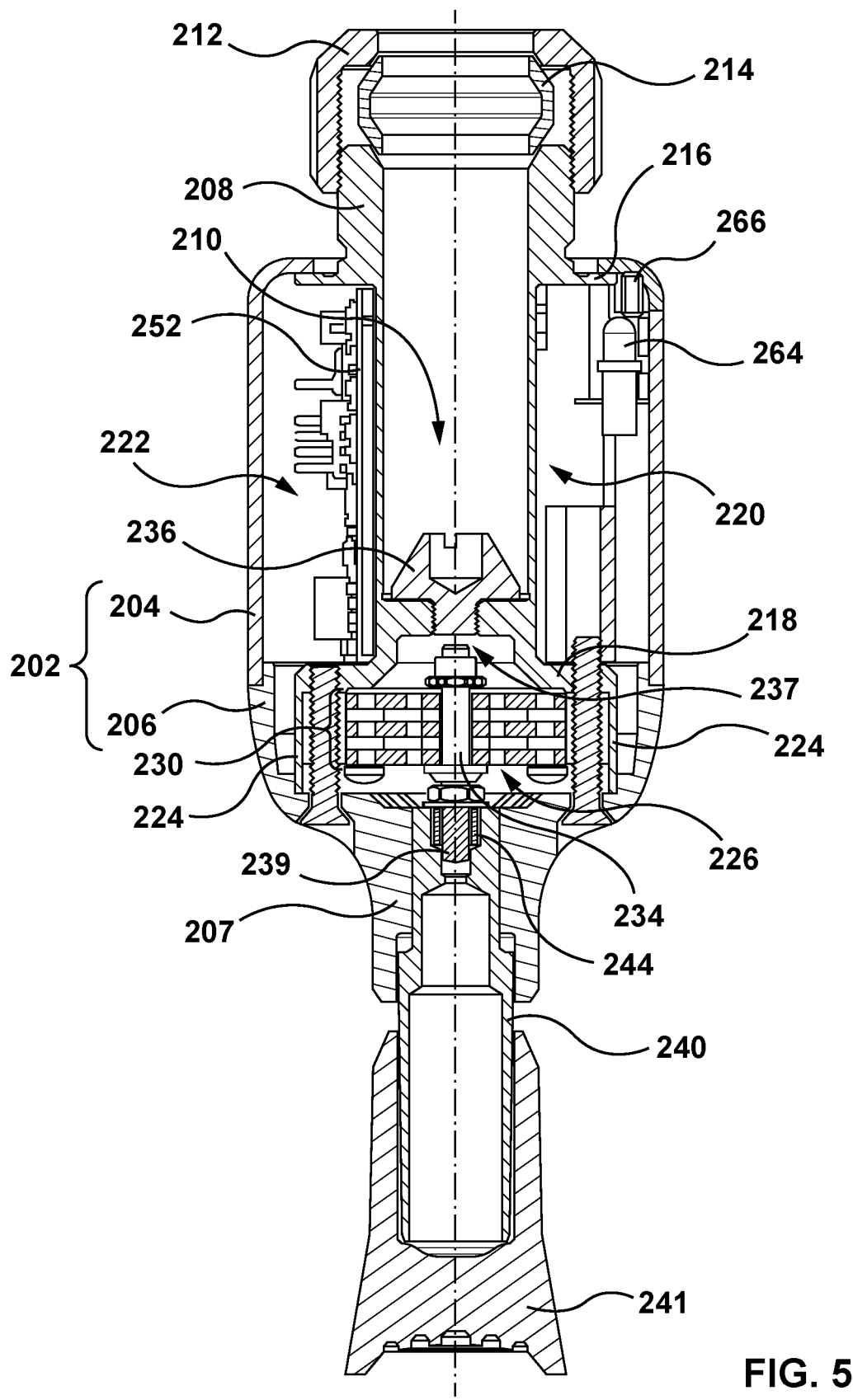
FIG. 5 is a primarily cross-sectional view of the smart crutch tip electronic device of FIG. 4 taken along line 5-5.
Figure 6:
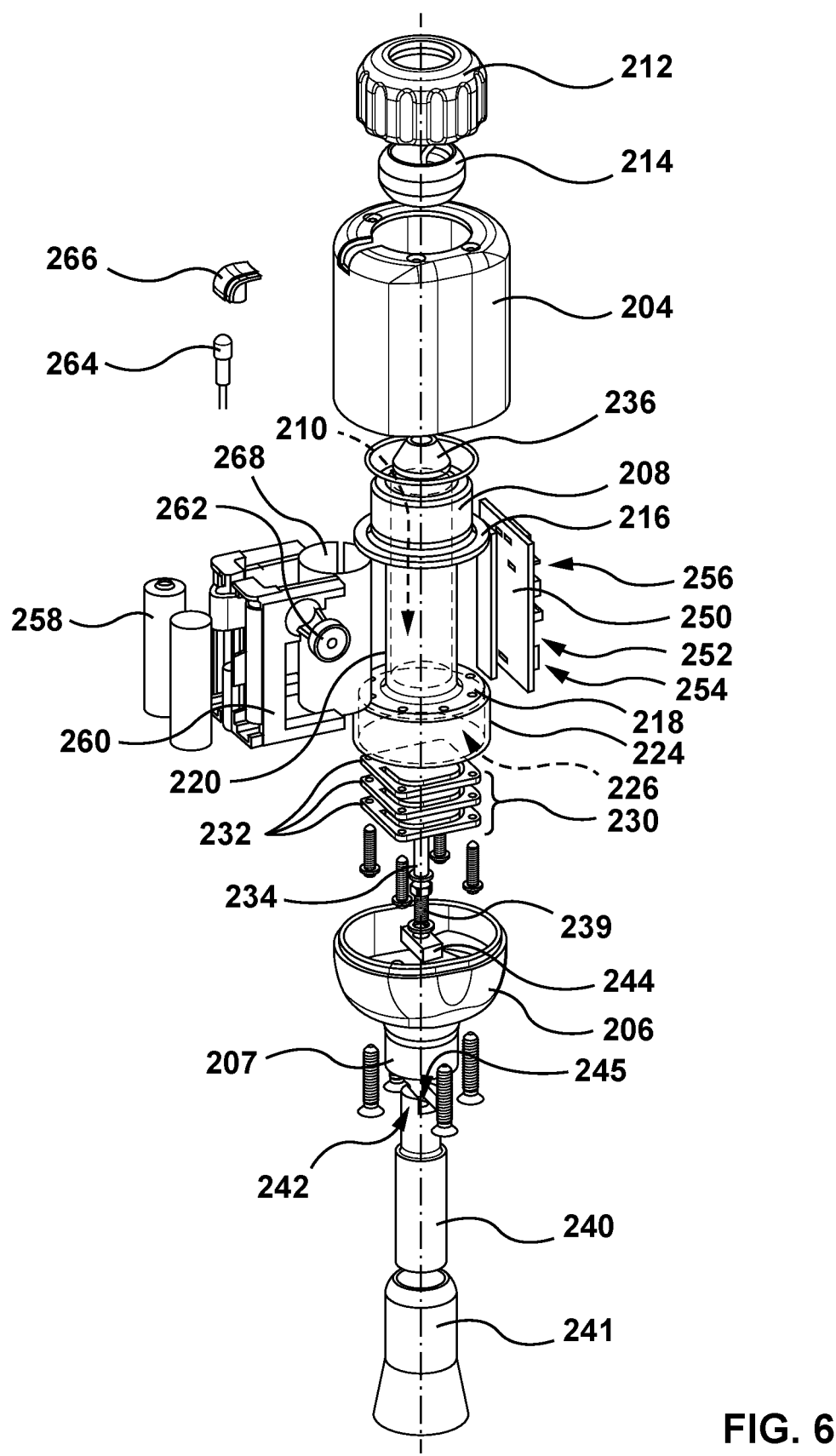
FIG. 6 is an exploded view of the smart crutch tip electronic device of FIG. 4.
Figure 7:
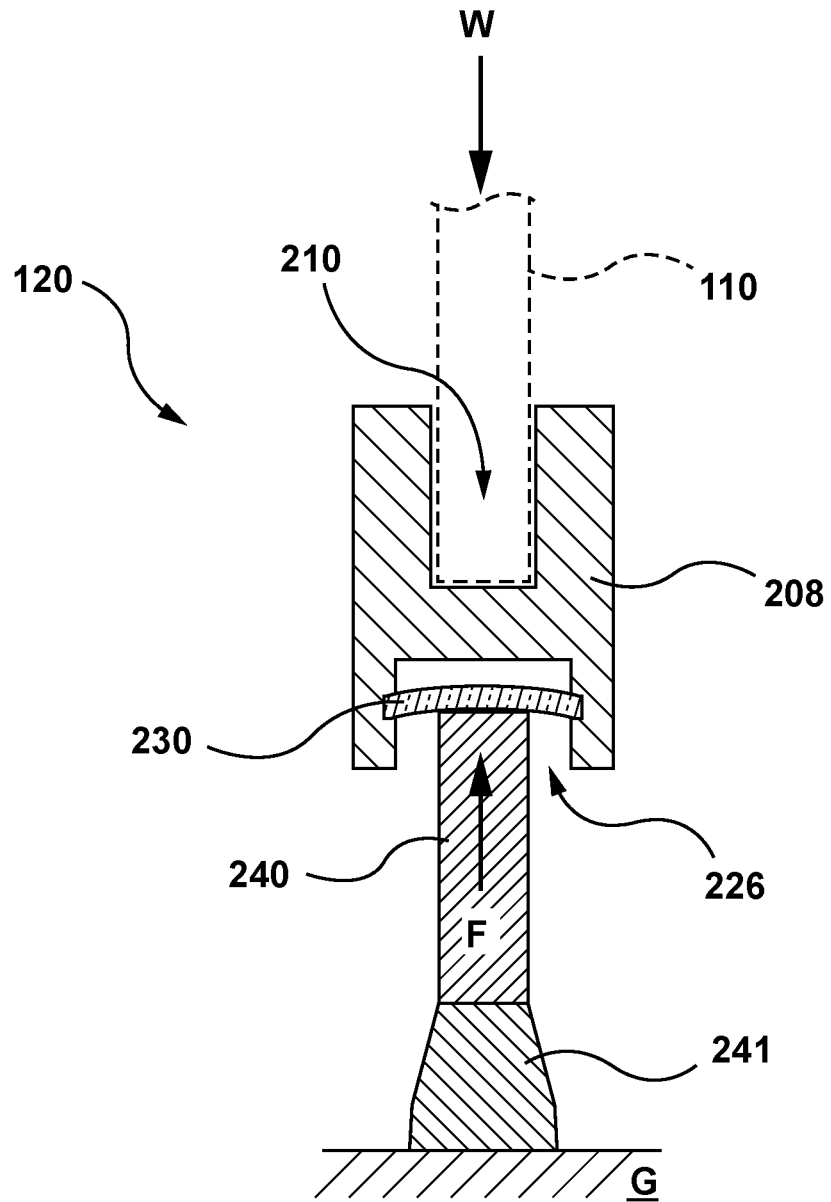
FIG. 7 is a simplified schematic cross-section of a lower portion of the smart crutch tip electronic device of FIG. 4.

As perhaps best seen in FIGS. 5 and 6, the body 208 defines receptacle 210 for receiving the tip of a leg of a walking aid, such as a crutch tip (i.e., the tip of a leg of the crutch), from above. A nut 212 and a resilient split ring 214 at the open end of the receptacle collectively serve as a retaining mechanism (or clamp or attachment means) for retaining the tip of the leg of the walking aid within the receptacle 210, i.e., for attaching the smart crutch tip 120 to the walking aid without tools, as will be described.

Referring to FIGS. 5 and 6, the body 208 of the present embodiment has a generally spool-like shape, with upper and lower annular flanges 216, 218 depending radially from either end of a central barrel portion 220. In the present embodiment, the barrel portion 220 is generally cylindrical, and the receptacle 210, which is also cylindrical in this embodiment, is coaxial with the barrel 220. The two flanges 216, 218 cooperate with the barrel 220 and the housing 202 to define an enclosed annular space 222 for safely housing electronic components, such as processor 252 (see, e.g., FIG. 5).

The body 208 includes an annular skirt 224 depending axially from a periphery of the lower annular flange 218, away from the barrel portion 220. The skirt 224 defines a hollow space 226 with an open end (see, e.g., FIG. 5). The hollow space 226 accommodates a load sensor 230, whose edges are anchored to the body 208 at skirt 224.

In the present embodiment, the load sensor 230 is an aggregation of three load sensor elements 232 held together with fastener 234 (e.g., a screw). The reason for aggregating multiple sensors 232 may be to aggregate a load-sensing capacity of multiple ones of the load sensor elements. Alternative embodiments may employ other load sensor arrangements, e.g., a single load sensor whose load-sensing capacity is sufficient for the purposes described herein.

A screw in the base of the receptacle 210 serves as an adjustable stop 236 to guard against possible load sensor damage that may result from excessive flexing of load sensor 230. The position of stop 236 may be adjusted by turning the screw to increase or decrease the size of a gap 237 above the load sensor 230 within which flexing can occur (see FIG. 6).

The funnel-shaped lower housing portion 206 has a tubular neck 207. The tubular neck slidably receives a base 240 having a rubber foot 241 at its lower end. The base 240, which is a cylindrical post in the present embodiment, is configured for limited axial movement (translation) with respect to the body 208 of the smart crutch tip 120 (vertically in FIG. 6).

A base stop 244 limits downward movement of the base 240 relative to the body 208 of the smart crutch tip 120. In the present embodiment, the base stop 244 is a cuboid rigid element that is attached to the base 240 using a bolt 239. More specifically, the base stop 244 is received within a notch 245 at the upper end 242 of the base 240, and a bolt 239 is passed through a central bore 243 of the base stop 244 and threaded into a vertical bore at the base of the notch 245. In the illustrated embodiment, the base stop 244 has a horizontal extent wider than that of the base 240, with the overhanging ends serving to limit downward movement of base 240 relative to body 208. The base stop 244 and bolt 239 may each be considered as an extension of the base 240 in this embodiment. Other forms of base stop could be used in alternative embodiments.

The load sensor 230 is disposed between the body 208 and the bolt 239 (and thus base 240, of which bolt 239 may be considered as a part). As such, the load sensor 230 is in the load path of the smart crutch tip 120. Specifically, in this embodiment, load passes between head of fastener 234 and the abutting head of bolt 239.

FIG. 7 is a schematic diagram illustrating a simplified model of a portion of the smart crutch tip 120. FIG. 7 may facilitate comprehension of the way in which smart crutch tip 120 can be used to measure a load upon a crutch 110, or other walking aid. For simplicity, FIG. 7 omits certain components of the smart crutch tip 120, such as the housing 202. Moreover, the components that are depicted are in simplified schematic form. For example, the base 240 and base stop 244 are depicted collectively as a single combined base element 240, again for simplicity.

Referring to FIG. 7, the tip (of the leg) of crutch 110 is received within the receptacle 210 and is retained therein by the nut 212 and the split ring 214 (not shown). When a patient applies weight W to the crutch 110, a downward force proportional to the applied weight W is transferred to the body 208 of the smart crutch tip 120. This downward force causes the body 208 to translate downwardly relative to the base 240 in respect of which the body 208 is axially translatable. The edges of load sensor 230, which are anchored to the body 208 within the hollow space 226, move with the body 208. A central area of the load sensor 230 transfers the downward force to an upper end of the base 240. However, the base 240 is prevented from moving downwardly by the ground G upon which the foot 241 sits. A resultant upward force F from the ground G is relayed by the base 240 (in this example, through bolt 239 see FIG. 6) and bears upon the central area of the load sensor 230 (in this example, upon fastener 234), causing the load sensor 230 to flex. The flexing causes the load sensor 230 to output a signal (data) indicative of the amount of weight W that is being borne by the crutch 110.

Referring again to FIGS. 5 and 6, the smart crutch tip 120 further includes a printed circuit board 250 with a processor 252 communicatively coupled to each of a memory 254 and a short-range wireless transceiver 256 (e.g., Bluetooth™ transceiver). The processor, memory, and transceiver may for example comprise a Bluetooth™ 5 module or Bluetooth™ BLE module, which may be a single integrated circuit component. The electronic components are powered by batteries 258 held by a battery holder 260, which also supports the printed circuit board 250 in this embodiment.

The memory 254 includes processor-executable instructions, e.g., firmware, that govern operation of the smart crutch tip 120 as described herein. The instructions may for example be loaded during manufacture of the smart crutch tip 120 and may be subsequently updated, e.g., via flashing.

The smart crutch tip 120 also includes an auditory notification element 262 (e.g., a buzzer), a visual notification element 264 (e.g., an LED protected by a transparent cover 266), and a speaker for providing voice notifications (not expressly depicted). These elements are for providing user feedback regarding target compliance directly from the smart crutch tip device itself. The mobile patient app 132 may also be configured to provide similar user notifications when in wireless communication range (e.g., Bluetooth™ LE range) of the smart crutch tip 120. If the body 208 is made from an electrically conductive material (e.g., aluminum), then a sheet of insulation 268 may be wrapped around the surface of barrel 220 to electrically isolate the printed circuit board 250, and other electrical components, from the body 208. Insulation 268 may be unnecessary when the body 208 is made from an electrically non-conductive material.

Referring again to FIG. 1, the crutches 110 may be one of a variety of types of crutches, such as axillary (underarm) crutches, elbow (lofstrand or Canadian) crutches, gutter (forearm support) crutches, or otherwise. Each crutch has a leg whose length may be adjustable to accommodate patients of different heights.

The mobile devices 130 and 140 (FIG. 1) may for example be smartphones carried by the patient 112 and the doctor 116 respectively, each having a touchscreen display for example. The computer 150 may for example be a laptop computer, desktop computer, or tablet used by the doctor 116.

The mobile doctor app 142 (FIG. 1) provides a mechanism for the doctor 116 to customize, prescribe, and optionally update lower extremity rehabilitation programs for one or more patients from the convenience of his mobile device 140. The mobile doctor app 142 also permits the doctor 116 to monitor the progress of a patient to whom a rehabilitation program has been prescribed. Monitoring can be performed in real time while the crutches 110 are being used. As will be described, monitoring is facilitated by graphical user interfaces (GUIs) by which the mobile doctor app 142 may efficiently display data regarding patient compliance with a prescribed rehabilitation program. The doctor web app 152 provides functionality like that of the mobile doctor app 142 but is web-based and thus platform-agnostic.

The mobile patient app 132 (FIG. 1) provides a mechanism for the patient 112 to receive a rehabilitation program designed by doctor 116 and to configure the smart crutch tips 120 to implement that rehabilitation program in the manner described herein. The mobile patient app 132 also receives usage data from the smart crutch tips 120, in real-time, indicating whether the crutches 110 are being used in accordance with the rehabilitation program. The patient 112 can efficiently display usage data in various ways using GUIs in the mobile patient app 132, as will be described. The usage data is also communicated back to the doctor 116 by way of the backend server application 162 for display within the mobile doctor app 142 and/or web-based doctor app 152, described above.

Operation of the system 100 will be described in the context of an example usage scenario. In this scenario, the patient 112 is a male who has suffered a lower extremity injury and has undergone surgery as a result. It presumed that the patient 112 has been referred to the doctor 116 for post-surgical rehabilitation. For example, the referral may be made verbally or in writing by a surgeon who performed the surgery. By way of the referral, the doctor 116 may be provided with unique patient contact information, such as a mobile telephone number or email address, and informed of the nature of the patient's lower extremity injury.

To prepare a rehabilitation program for the patient 112, the doctor 116 may invoke the mobile doctor app 142 on his mobile device 140. The app 142 may have been downloaded to the doctor's mobile device 140 from an app store, such as Google™ Play or the Apple™ App Store for example. The doctor may have completed a registration procedure upon initial app invocation, e.g., specifying information that may include the doctor's name, location, professional specialization, experience, workplace, and telephone number.

If the patient 112 is a new patient, the doctor 116 may initially use the app 142 to create a new patient record. A patient record, which may be referred to as a "patient card", may be considered as a digital representation of a patient file maintained in the context of a lower extremity rehabilitation. The mobile doctor app 142 may permit the user to create multiple patient records to permit the user to oversee the rehabilitation of multiple patients in parallel.

Creation of a new patient card may entail three steps.

In a first step, the app 142 may prompts the doctor 116 to enter unique patient contact information for patient 112, such as a mobile telephone number or an email address.

In a second step, the app 142 may prompt the doctor 116 to specify the type of lower extremity injury that has been suffered. For example, the app 142 may display GUI that includes a radio button (or other user input mechanism) with two mutually exclusive options: a "surgery" option and a "therapy" option. For the present scenario, the surgery option may be chosen to indicate that the patient 112 has undergone surgery. The therapy option may be chosen in scenarios in which a lower extremity injury has been suffered but no surgery has been performed.

The GUI may further prompt the doctor to enter specifics regarding the injury, e.g., via several pull-down lists (or other user input mechanism). One pull-down list may be used to identify the lower extremity that has been injured, which in this example is the left hip joint. Another pull-down list, which may appear only in the case where the surgery option was chosen, may specify the type of surgery that was performed (e.g., metal osteosynthesis in this example). A further pull-down list may be used to precisely identify the injury that was initially suffered (e.g., a fracture of the femoral neck in this example).

Figure 8:
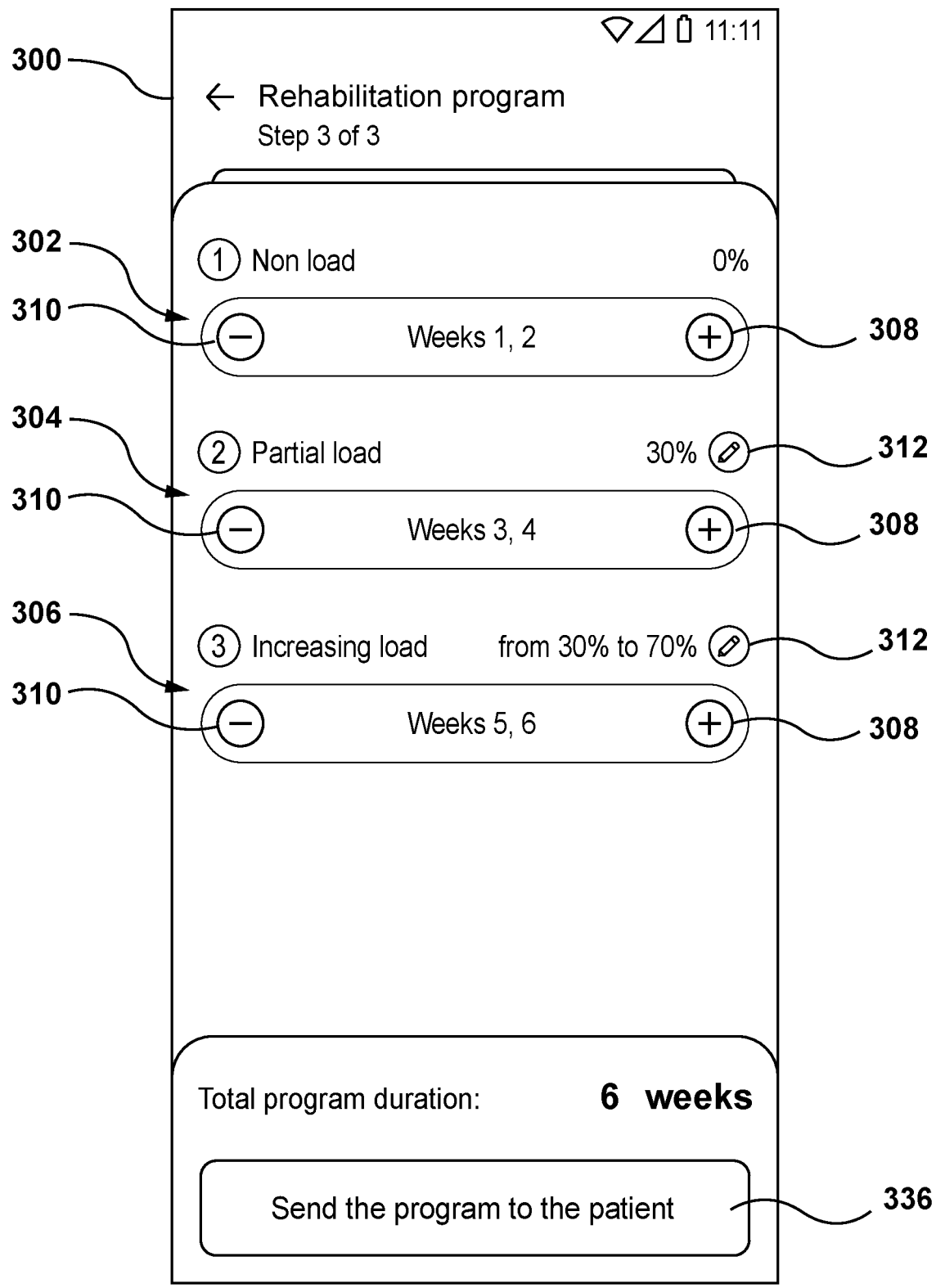
FIG. 8 depicts a graphical user interface (GUI) displayed by a mobile patient software application at a patient mobile device of FIG. 1.

In a third step, the doctor app 142 may prompt the doctor 116 to specify and/or customize the parameters of a rehabilitation program. To that end, the mobile doctor app 142 may display a GUI 300 as shown in FIG. 8. In the depicted embodiment, the GUI 300 permits the rehabilitation program to be specified in terms of one, and possibly multiple, rehabilitation phases. For each phase, the doctor 116 is prompted to specify the following parameters: the type of loading that should be performed on the injured lower extremity during that phase (zero load, constant load, or steadily increasing load); the duration of the phase; and the percentage of body weight to apply to the injured lower extremity during that phase. Each phase that is specified by the user is represented as a numbered entry in GUI 300. In alternative embodiments, other GUI formats could be used.

In the example GUI 300 depicted in FIG. 8, the doctor 116 has specified a six-week rehabilitation program having three phases. A first numbered entry 302 displayed in GUI 300 represents a first, "non load" (i.e., 0% loading) phase, whose duration has been set to two weeks. A second numbered entry 304 represents a second, constant load phase, also having a duration of two weeks, during which 30% body weight should be applied to the injured lower extremity. A third numbered entry 306 represents a third, increasing load phase, also having a duration of two weeks, during which the body weight applied to the injured lower extremity should increase progressively from 30% to 70%. In GUI 300, the numerical order of the entries, i.e., their relative ordinal positions, specifies the chronological order in which the phases should be performed during the rehabilitation program.

In the example GUI 300 of FIG. 8, the "+" (plus) icon 308 and "−" (minus) icon 310 depicted in each entry are user input mechanisms whose selection either increases or decreases, respectively, a duration (here, in weeks) of the phase that is represented by the entry in association with which the icons are displayed. A phase may be eliminated by setting its duration to zero weeks. Moreover, the doctor 116 may use the "edit" icons 312 to change the percentage of loading, e.g., in increments of 10%, for the phase represented by the entry in which the icons are displayed. Notably, the degree of loading is expressed in relative terms, e.g., as a percentage (fraction) of total body weight, rather than in absolute units such as pounds, since the doctor 116 may not have any indication of the patient's weight at this stage.

Once the rehabilitation program has been customized as the doctor 116 sees fit, selection of the "send the program to the patient" button 336 (or similar GUI construct) may cause two steps to be performed.

Firstly, data 143 indicative of the specified rehabilitation program parameters may be communicated to the backend server application 162 along with a unique patient identifier, e.g., the unique patient contact information (see FIG. 1). The backend server application 162 may create a patient database record (not expressly depicted) containing this rehabilitation program parameter data 143, indexable by the unique patient identifier. This step may occur transparently from the perspective of the doctor 112. The data 143 in this example includes, for each of a plurality of time intervals (here, days) spanning a rehabilitation period (here, six weeks), a target relative load on an injured lower extremity during the time interval (here, expressed as a percentage) relative to a patient body weight.

Secondly, the earlier-specified patient contact information may be used to send a communication to the patient 112, e.g., via SMS (text message) or email, to advise that a rehabilitation program has been prepared for that patient. The communication may include a URL (link) whose selection by patient 112 may trigger a download of the mobile patient app 132 to the mobile device 130.

Upon being installed and invoked at the mobile device 130, the mobile patient app 132 may prompt the patient 112 to complete patient registration by entering data including name, gender, date of birth, and weight information. It will be appreciated that entry of an indication of patient body weight is required to permit the mobile patient app 132 to convert the relative (percentage) lower extremity target loads specified by doctor 116 within the rehabilitation program parameter data 143 to absolute target loads (e.g., in pounds or kilograms) that the smart crutch tips 120 will be capable of measuring, as will be described.

At the completion of patient registration, the mobile patient app 132 may communicate the collected patient information to the backend server application 162. The backend server application 162 may add that information to the patient database record maintained at the cloud-based server 160.

Based on the presence of rehabilitation program parameter data 143 in the patient database record, the mobile patient app 132 may notify the patient 112 that a rehabilitation program has been prepared by the doctor 116. Upon receiving approval from the patient 112, the rehabilitation program parameter data may 143 be communicated to the mobile device 130 for use by the mobile patient app 132.

At this stage, the patient 112 may acquire the pair of smart crutch tips 120, e.g., from the doctor 116 or another source. The crutches 110 may already in the possession of the patient 112 or may be newly acquired along with the smart crutch tips 120.

One of the smart crutch tips 120R may then be installed onto the tip of a leg of the right crutch 110R, and the other smart crutch tip 120L may be installed onto the tip of a leg of the second crutch 110L. Installation (attachment) may entail removing a rubber foot from each crutch leg, inserting the tip of the crutch leg through the nut 212 and into the receptacle 210 of the respective smart crutch tip 120, and tightening of the nut 212 to attach the body 208 the smart crutch tip 120 to the crutch 110. The smart crutch tips 120R, 120L may be considered to be associated with the crutches 110R, 110L, respectively, onto which they have been, or will be, installed. Each of the smart crutch tips 120 may then be activated using a power button (not expressly depicted).

Figure 9:
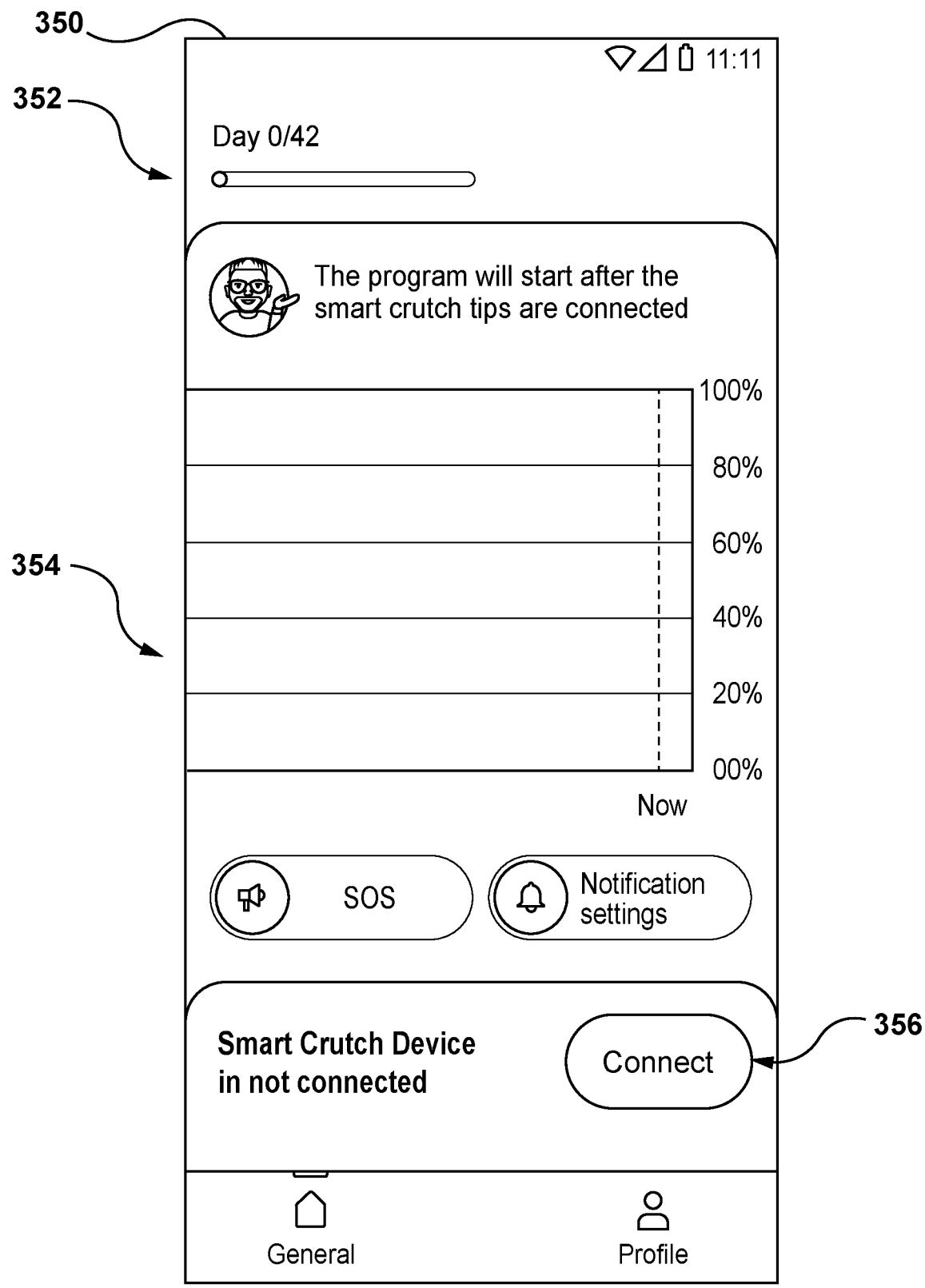
FIG. 9 depicts a GUI displayed by a mobile doctor software application at a doctor mobile device of FIG. 1.

At this stage, the mobile patient app 132 may display a GUI 350 as shown in FIG. 9. This GUI 350 may be considered as a main GUI screen of the mobile patient app 132 by which the patient 112 can monitor daily progress through the rehabilitation program. As illustrated, the main GUI 350 includes a progress bar 352 showing how much of the lower extremity rehabilitation program has been completed. In this embodiment, a textual indicator "Day 0/42" indicates that the patient 112 has not yet commenced the six-week (42-day) rehabilitation program. A recent usage history display area 354 may accordingly be blank as shown in FIG. 9.

To establish a wireless connection between the mobile device 130 and the smart crutch tips 120 by which data may be exchanged, the user may be prompted to select a "Connect" button 356 or similar GUI construct. In the present embodiment, selection of this button may trigger a BlueTooth™ LE pairing process between the mobile device 130 and one of the smart crutch tips 120R that has been predesignated as the "primary" smart crutch tip that will be responsible for communication with the mobile device 130 on behalf of the pair of smart crutch tips 120R, 120L. For example, upon selection of the "connect" button 356, the mobile device 130 may scan for any BlueTooth™ LE advertising packets being wirelessly broadcast by any nearby smart crutch tip devices. In so doing, the mobile device 130 will detect the proximity of primary smart crutch tip 120R and may identify that device as being proximate. Upon user confirmation that connection should proceed, the two devices may exchange security keys and establish a data communication channel.

In the present embodiment, the mobile device 130 does not communicate directly with the other, secondary smart crutch tip 120L. The reason is that the primary smart crutch tip 120R is solely responsible for communicating with the mobile device 130 on behalf of the pair of smart crutch tips 120 in this embodiment. The secondary smart crutch tip 120L will communicate information about the dynamic load upon associated left crutch 110L, wirelessly in real time, to the primary smart crutch tip 120R. In turn, the primary smart crutch tip 120R will use the information from the secondary smart crutch tip 120L, together with locally measured dynamic load information upon associated right crutch 110R, to calculate the collective load on the pair of crutches 110 in real time, as will be described. It is the collective load information that will be communicated to the mobile device 130.

The primary smart crutch tip 120R of the present embodiment is operable to automatically establish a wireless connection with the secondary smart crutch tip 120L, e.g., soon after the devices 120R, 120L are powered up. This may be done via a short-range wireless communication mechanism such as Bluetooth™. In one embodiment, a unique Media Access Control (MAC) address of the secondary smart crutch tip 120L may be preprogrammed into the firmware of the primary smart crutch tip 120R, e.g., during manufacture, to facilitate such automatic establishment of the wireless connection, transparently from the perspective of the user.

After some predetermined number of steps has been taken (e.g., five steps), the rehabilitation program may be considered to have commenced. The current date at the mobile device when this occurs may be deemed as the first day of the rehabilitation period.

The mobile patient app 132 may use the rehabilitation program parameter data 143 originating from the doctor 116 and the patient body weight information specified locally by the patient 112 to generate and output rehabilitation program data 144 for configuring the smart crutch tips 120. The rehabilitation program data 144 specifies patient-specific absolute target loads for the pair of crutches 110 for each day of the rehabilitation program. In effect, the rehabilitation program data 144 defines a schedule for use by the smart crutch tip 120, which specifies a target (absolute) load for the walking aid for each day of the rehabilitation period. A calendar date may be computed and stored with each of the daily target loads (of which there are 42 in the present embodiment), to indicate when each target load will be operative. Creation of the array may be triggered by the patient 112 in the mobile patient app 132. Alternative embodiments could employ other data structures besides an array (e.g., a linked list of records).

It will be appreciated that expressing the targets as absolute weight targets for the crutches, rather than as absolute weight targets for the injured lower extremity, facilitates use of the smart crutch tips 120 to monitor rehabilitation program compliance by patient 112 in real time. The reason is that the smart crutch tips 120 directly measure the load on the crutches rather than directly measuring a load on the injured lower extremity.

In the present embodiment, the rehabilitation program data 144 is expressed as an array of N elements, where N is a positive integer indicating a number of time intervals into which the rehabilitation period has been divided. In the present embodiment, each of the N elements represents a single day of the rehabilitation program and contains a value indicating a target load for the pair of crutches for that day, in absolute units (e.g., pounds or kilograms). The rationale for using a single day as the time interval is that patients may expect that their use of the walking aid over the course of a single day should be consistent, i.e., should target the same load throughout the day. It is possible that the rehabilitation program data 144 in alternative embodiments could specify target loads for time intervals that are shorter than or longer than one day. In general, the term "time interval" as used herein refers to a finite period of time, be it one day or otherwise.

FIG. 10 depicts example rehabilitation program data 144 that may be generated by the mobile patient app 132 from the example rehabilitation program parameters specified in FIG. 8. The loads in FIG. 10 assume a patient-specified weight of 200 pounds. As illustrated, the data 144 comprises an array of 42 elements. Each element is identified in FIG. 10 by a reference numeral that is the ordinal day number of the 42-day (six week) rehabilitation program preceded by "144-". For example, array element 144-3 contains the target load for the pair of crutches 110 for the third day of the rehabilitation program. The associated calendar date of Jan. 20, 2021 for that day (expressed in format MM/DD/YY in FIG. 10) may also be stored in the array element 144-3.

It will be appreciated that elements 144-1 to 144-14 of FIG. 10 correspond to phase 1 of the rehabilitation program (entry 302 of FIG. 8), elements 144-15 to 144-28 of FIG. 10 correspond to phase 2 of the rehabilitation program (entry 304 of FIG. 8), and elements 144-29 to 144-42 of FIG. 10 correspond to phase 3 of the rehabilitation program (entry 306 of FIG. 8). From the perspective of the smart crutch tip 120, however, there may be no awareness of the existence of any phase(s). The reason is that the smart crutch tip 120 does not require phase information to be able to provide immediate user feedback regarding target load compliance via visual, auditory, or voice notifications. In contrast, the mobile patient app 132 does maintain phase information, so that more sophisticated usage analytics may be provided to the patient 132 on request.

To compute the crutch target loads expressed in pounds for each of the 42 elements of array 144, the mobile patient app 132 may first compute the lower extremity target load in pounds for each day. This may be done by multiplying the target percentage load on the lower extremity, as specified by the doctor 116 for the relevant day, by the patient weight of 200 pounds. The resultant values may then be subtracted from the patient weight to calculate daily crutch target loads, i.e., to calculate, for each of the plurality of time intervals spanning the rehabilitation period, a target absolute load on the walking aid during the time interval. In this example, the target loads are expressed in pounds, e.g., for consistency with the unit of measure of the load sensor 230 (which is assumed to be pounds the present example).

It will be appreciated that the progressively decreasing target load values in array elements 144-29 to 144-42 correspond to the progressively increasing phase 3 lower extremity target load of 30%-70% of body weight. The target load values in the array may be computed as follows. First, the change in absolute weight on the lower extremity during this phase may be calculated: (70%-30%)*200 lbs.=80 lbs. Then that change in absolute weight may be broken into fixed daily increments for the number of days in the phase (e.g., increments of 6.15 lbs. in this example). Then the crutch target load for each day of the phase may be set to the previous day's target load less that amount. In the present embodiment, target loads in array 144 are rounded to the nearest pound, although such rounding is not absolutely required.

Once the mobile patient app 132 has generated the rehabilitation program data 144 (array in this example), the data 44 is wirelessly transmitted to the primary smart crutch tip 120R. As earlier noted, one smart crutch tip 120R is predesignated as the primary and the other smart crutch tip 120L is predesignated as the secondary. The primary smart crutch tip 120R is responsible not only for measuring the dynamic load on its own respective crutch 110R for each detected step but also for combining that dynamic load data with the dynamic load data received wirelessly from the other, secondary crutch to compute a peak load for the pair of crutches 110. The secondary smart crutch tip 120L is only responsible for measuring the dynamic load on its respective crutch 110L for each patient step and for wirelessly communicating that information to the primary. The secondary smart crutch tip 120L does not directly communicate with the mobile device 130 in this embodiment. In this arrangement, the rehabilitation program data 144 is stored only at the primary smart crutch tip 120R. The smart crutch tips 120R, 120L that are designated as primary and secondary may be on either crutch and on either side of the patient's body.

Figure 11:
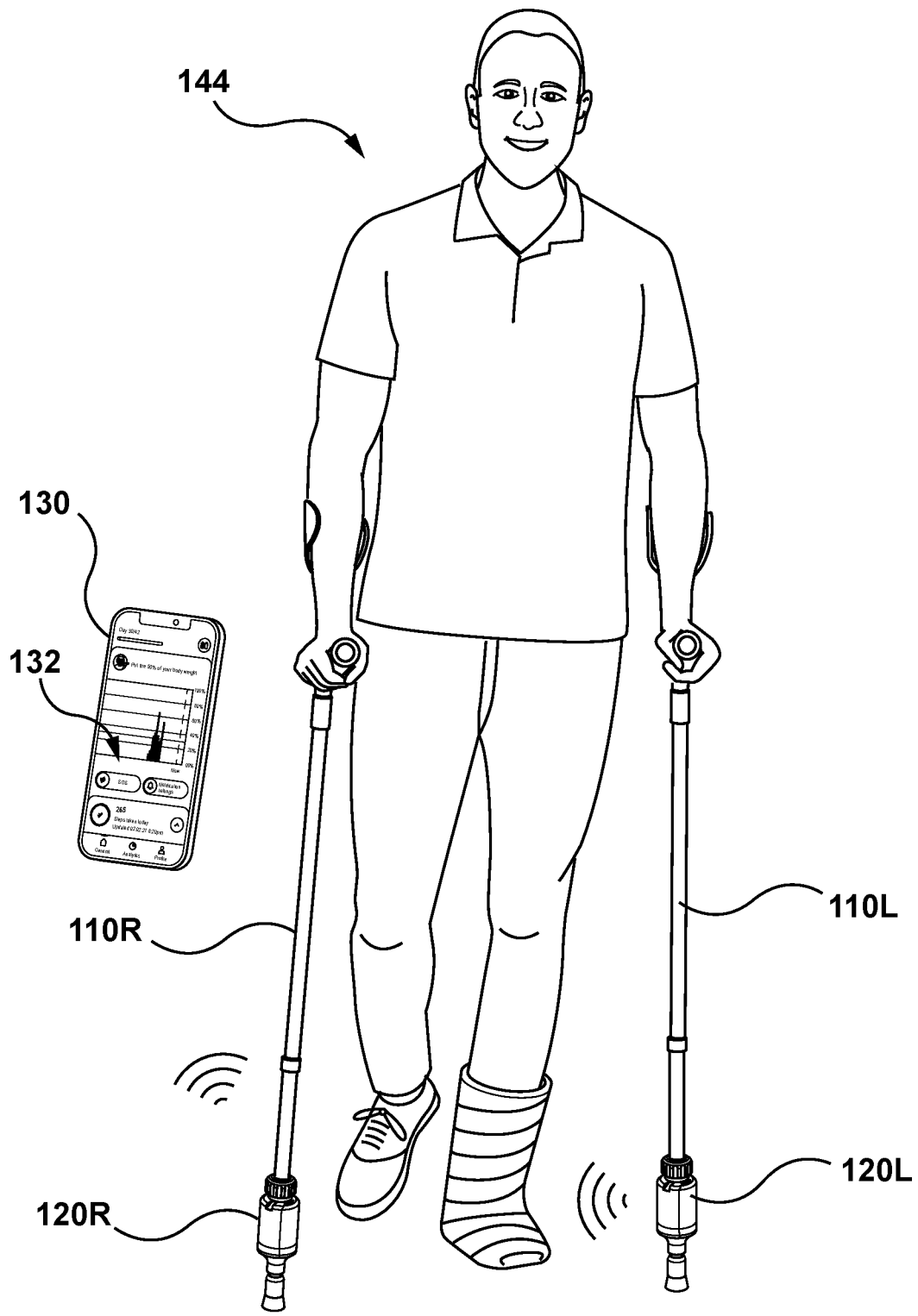
FIG. 11 is a perspective view of the smart crutch tip devices of FIG. 1 installed onto crutches and ready for use.

At this stage, the crutches 110 are ready for use by the patient 112, e.g., as shown in the perspective view of FIG. 11.

Figure 12:
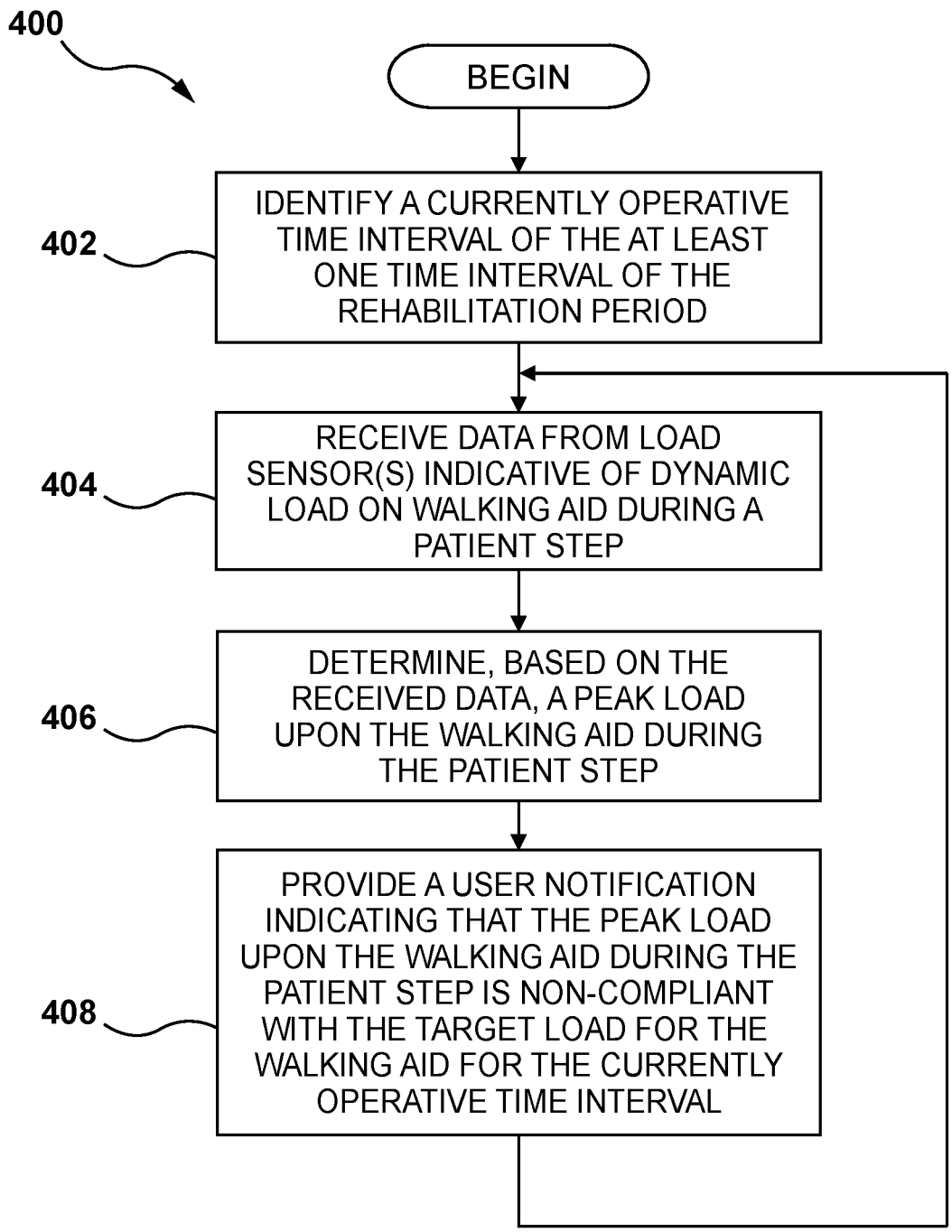
FIG. 12 is a flowchart of operation of the primary smart crutch tip of FIG. 1 for monitoring compliance with a currently operative target load.
Figure 13:
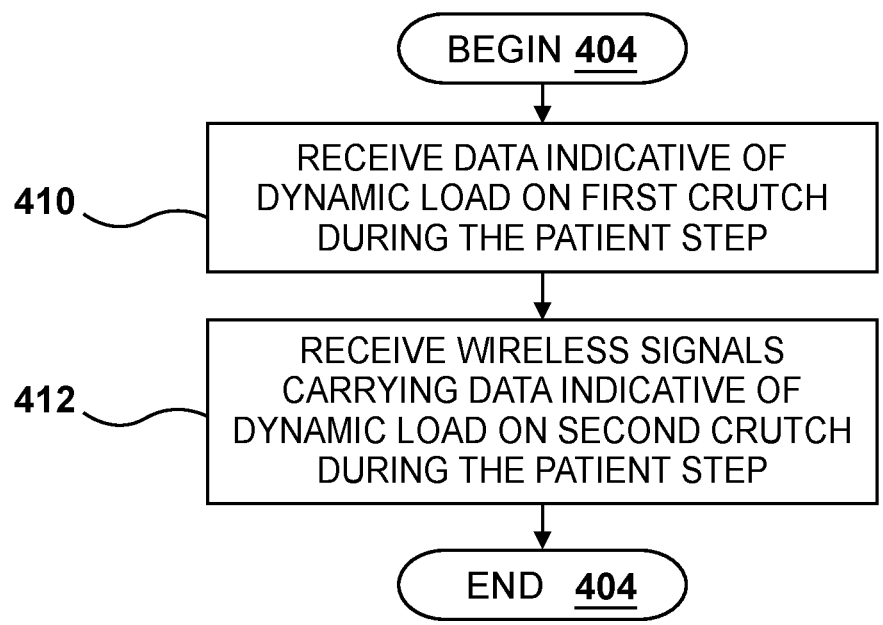
FIG. 13 is a flowchart providing detail regarding one of the operations of FIG. 12 in the case where the walking aid comprises two crutches.
Figure 14:
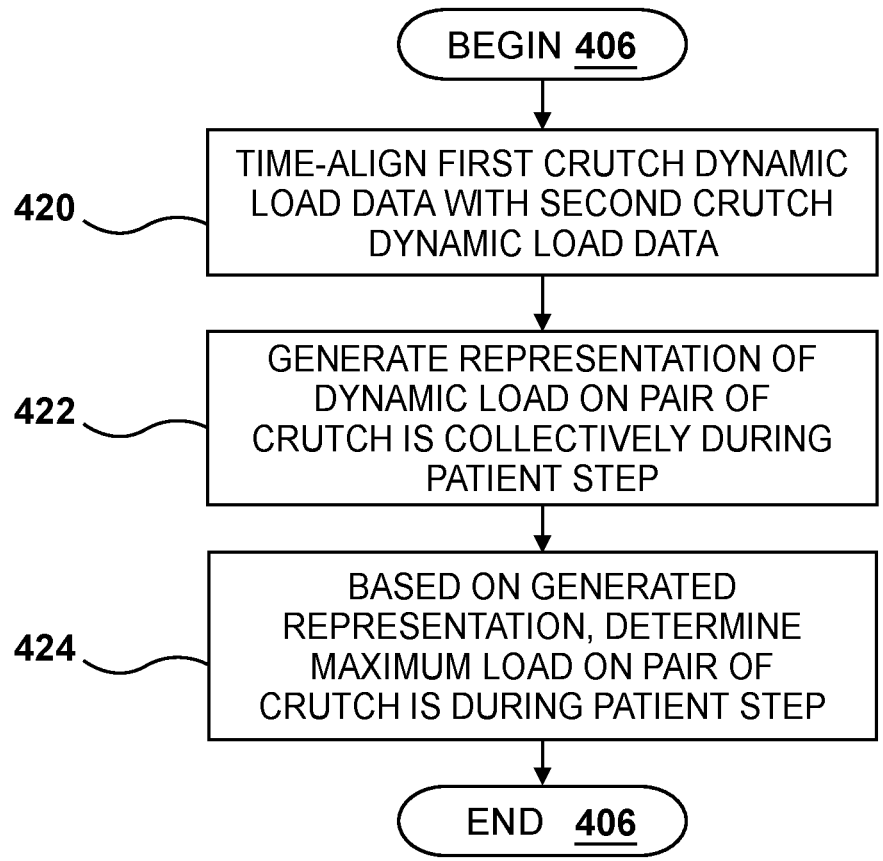
FIG. 14 is a flowchart providing detail regarding another one of the operations of FIG. 12 in the case where the walking aid comprises two crutches.
Figure 15A:
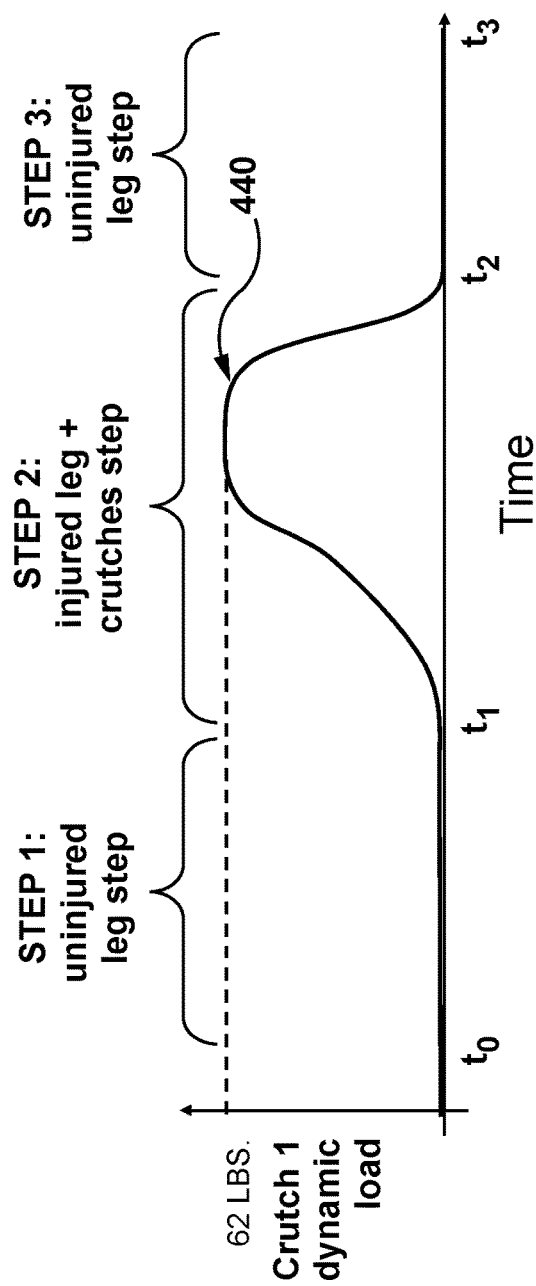
FIG. 15A is a line graph depicting the dynamic load on a first crutch of the pair of crutches shown in FIG. 1 during a patient step.
Figure 15B:
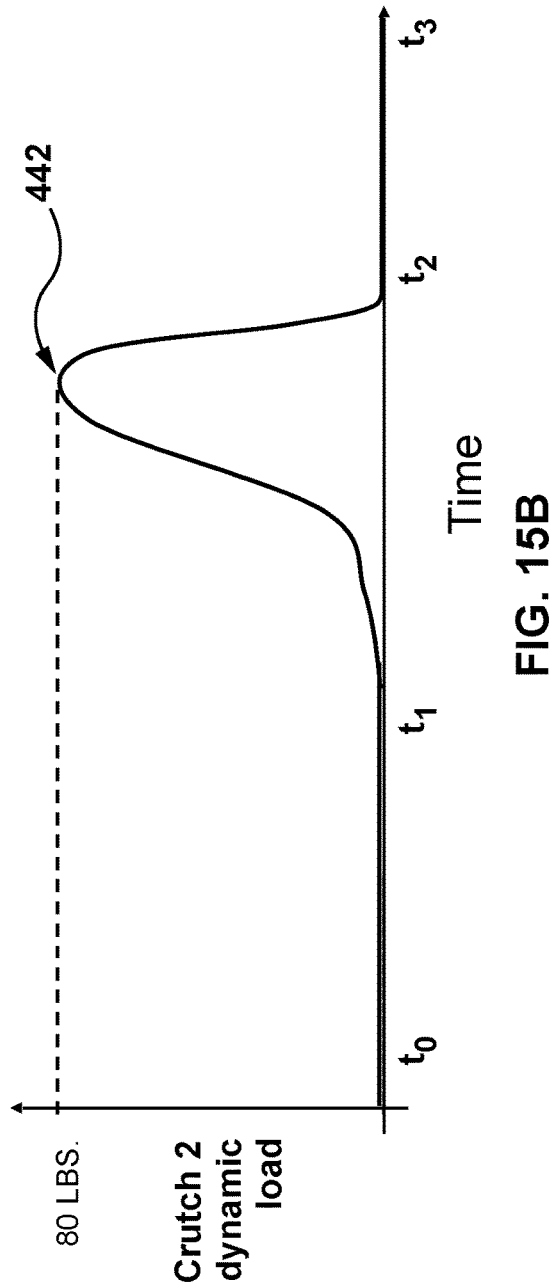
FIG. 15B is a line graph depicting the dynamic load on a second crutch of the pair of crutches shown in FIG. 1 during the same patient step.
Figure 16:
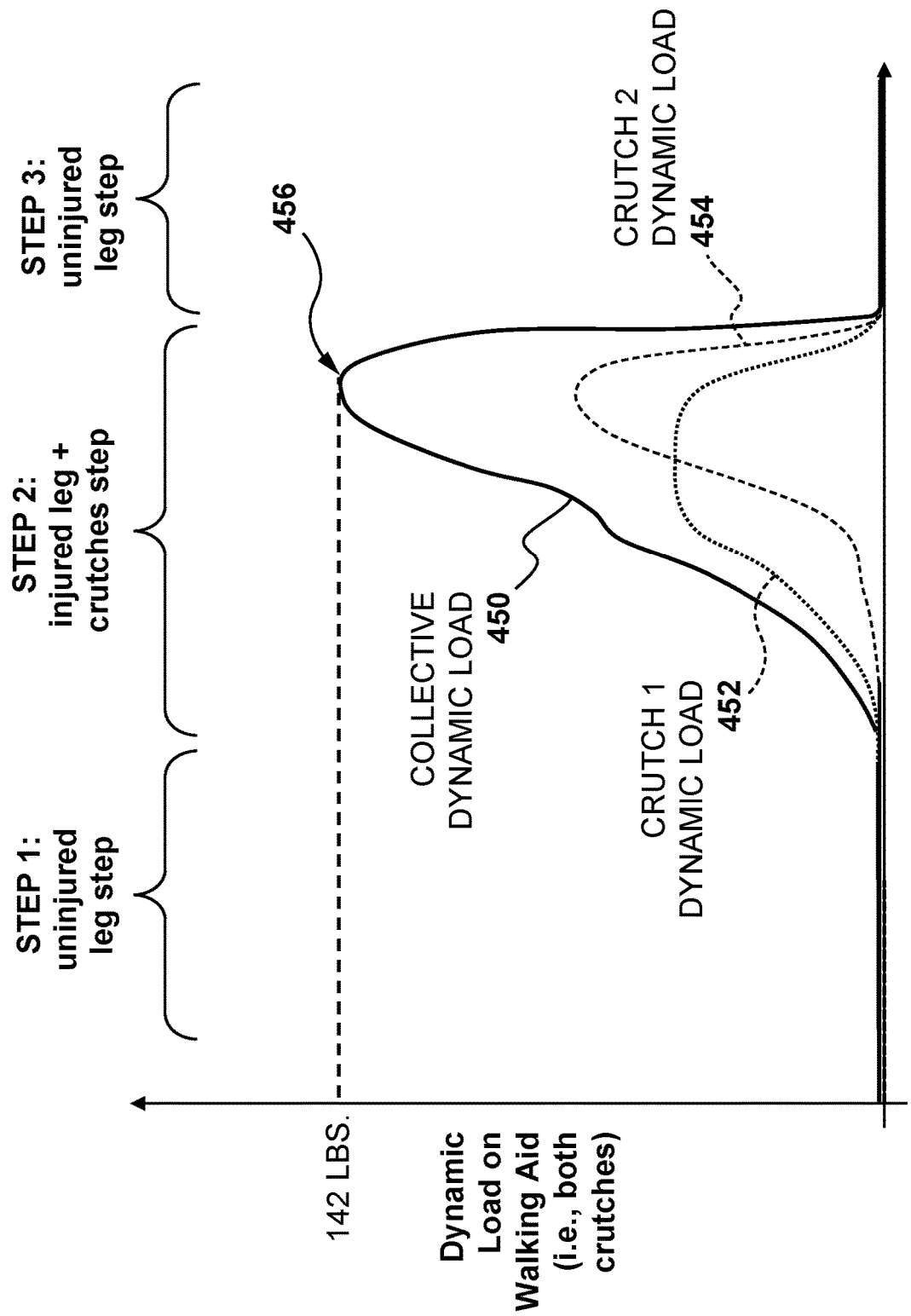
FIG. 16 is a line graph depicting the dynamic load on the pair of crutches shown in FIG. 1 collectively during the patient step.

Operation of the smart crutch tips 120 for monitoring compliance with a weight-bearing target of a lower extremity rehabilitation program is depicted in FIGS. 12-16. FIG. 12 is a flowchart of operation 400 of the primary smart crutch tip 120R for monitoring compliance with a currently operative target load during the rehabilitation program. Operation 400 may be triggered whenever motion is detected at the smart crutch tip 120R, e.g., using an accelerometer (not expressly depicted). FIGS. 13 and 14 are flowcharts providing detail regarding certain operations of FIG. 12 in the case where the walking aid comprises two crutches. The operations in FIGS. 12, 13, and 14 may be effected largely or entirely in software, which may be stored in memory 254 and executed by processor 252. The software may for example be firmware. FIG. 15 illustrates the dynamic load data measured by each of smart crutch tip 120R and smart crutch tip 120L during an example patient step. FIG. 16 illustrates the total dynamic load on the pair of crutches 110 during the same patient step.

For the purpose of FIG. 12, it is presumed that the primary smart crutch tip 120R has already received, and has stored in its memory 254 (see FIG. 6), the array of rehabilitation program data 144 depicted in FIG. 10. It will be recalled that this data 144 corresponds to the six-week rehabilitation program customized by the doctor 116 using the GUI 300 of FIG. 8. The rehabilitation program is presumed to have been commenced on Jan. 18, 2021. It is also presumed that the clocks of the processors 252 on the two smart crutch tips 120R, 120L have been synchronized. This may for example occur at the time that the wireless connection between the smart crutch tips 120R, 120L is first established.

In operation 402 (FIG. 12), a currently operative time interval of the at least one time interval of the rehabilitation period is identified. In the present embodiment, identification of the currently operative time interval is based on the current date. More specifically, the processor 252 of the primary smart crutch tip 120R determines the current date. This may for example be done in software via a suitable operating system API call. Alternatively, the current date may be transmitted by the mobile device 130 to the primary smart crutch tip 120R at the time that a wireless connection is established between the two devices.

In this example, it is presumed that current date that is determined in operation 402 is Feb. 2, 2021. Using this information as a lookup into the array 144 of FIG. 10, the primary smart crutch tip 120R identifies the 16th day of the 42-day rehabilitation period, represented by array element 144-16, as the current day—or, more generally, as the currently operative time interval—of the rehabilitation period. In other words, it is presumed that patient 112 has already been using the smart crutch tips 120 for 15 days. The processor 252 may then read the value contained in that array element, i.e., 140 pounds, and may update a "current target load" variable to indicate the target for the current day.

In operation 404 (FIG. 12), data is received from one or more load sensors indicative of a dynamic load on the walking aid during a patient step. For the present scenario, in which the walking aid comprises multiple units (two crutches 110), operation 404 may entail the steps shown in FIG. 13.

Referring to FIG. 13, in step 410, the primary smart crutch tip 120R receives data from load sensor 230 indicative of a dynamic load on the first crutch 110R during a patient step. A step may be considered to have occurred when processor 252 of the primary smart crutch tip 120R detects the following pattern output by the load sensor 230: zero load followed by a positive load followed by zero load. For this example, it is assumed that the dynamic load is as depicted in FIG. 15A.

FIG. 15A is a line graph depicting the dynamic load measured by the load sensor 230 of the primary smart crutch tip 120 during the three patient steps shown in FIG. 2. Load is represented by the vertical axis, and time is represented by the horizontal axis. For step 410, it is presumed that the processor 252 receives data corresponding to the dynamic load between time t1 and time t2 of FIG. 15A. The data may be sampled at a predetermined frequency to generate a digital representation of the line graph of FIG. 15A. The digital representation may be recorded with timestamp information indicating when the samples were taken. As shown in FIG. 15A at 440, the maximum load measured on the first crutch 110R during step 2 is 62 pounds.

In step 412 of FIG. 13, the primary smart crutch tip 120R receives wireless signals carrying data indicative of a dynamic load on the second crutch 110L during the same patient step. The secondary smart crutch tip 120L may use the same approach as the first crutch to determine when a patient step has been taken and to sample the load on the second crutch 110L during the step. The dynamic load on the second crutch is presumed to be as shown in FIG. 15B, with a maximum load of 80 pounds shown at 442. The samples capturing the dynamic load on the second crutch may be transmitted via Bluetooth™ LE to the primary smart crutch tip 120R along with associated timestamp information indicating when the samples were taken.

It will be appreciated that the maximum load on the second crutch during the step, i.e., 80 pounds, is greater than the maximum load on the first crutch during that step, i.e., 62 pounds. Such discrepancies in load between crutches may arise, e.g., when the patient 112 leans more heavily on one crutch than on the other while taking a step.

Referring again to FIG. 12, in operation 406, the smart crutch tip 120R determines, based upon the received data, a peak load upon the pair of crutches 110 collectively during the patient step. For the present scenario, in which the walking aid comprises two crutches 110, operation 406 may entail the steps depicted in FIG. 14.

In step 420 (FIG. 14), first crutch dynamic load data is time-aligned with the second crutch dynamic load data. This step may entail using timestamp information to identify pairs of load samples that were taken substantially simultaneously at the smart crutch tips 120R, 120L, respectively.

In step 422 (FIG. 14), a representation of the dynamic load on the pair of crutches collectively during the patient step is generated. This step may entail summing the time-aligned samples from the two smart crutch tips 120R, 120L to generate a representation of total load on both crutches 110R, 110L. In the present example, this may result in a digital representation of the line 450 shown in FIG. 16.

FIG. 16 is a line graph whose axes are analogous to those of FIGS. 15A and 15B. Dashed lines 452 and 454 represent dynamic load data for crutch 1 and crutch 2, respectively, as depicted in FIGS. 15A and 15B, respectively. Line 450 represents a summation of lines 452 and 454, which may be the result of step 422 of FIG. 14. It will be appreciated that the time-aligning is performed so that the summing will accurately reflect the total load on the crutches 110 at the relevant times.

In step 424 (FIG. 14), the maximum load of the representation (sum) generated in step 422 is determined. Referring to FIG. 16, the maximum load 456 for the step taken between time t1 and time t2 is determined to be 142 pounds. This load may be considered as the peak load on the pair of crutches 110R, 110L during the patient step.

Referring again to FIG. 12, in operation 408, a user notification is provided indicating whether the peak load upon the walking aid during the patient step, as determined in operation 406, is non-compliant with the target load for the currently operative time interval, i.e., day 16 of the six-week rehabilitation program. In the present embodiment, the patient 112 is considered to have complied with the target load if the peak load is within a range that is centered on the current target load and whose limits are 10% greater than and 10% less than the target load.

In the present example, the target load for the current date of Feb. 2, 2021, is 140 pounds (see element 144-16 of FIG. 10), so the range of weights that are considered compliant is 126 lbs. to 154 lbs. Because the peak load of 142 lbs. determined in operation 406 is within that range, no user notification is provided.

Had the peak load from operation 406 been greater than 154 lbs., meaning that too much weight was on the crutches 110 and not enough weight was on the injured lower extremity, the primary smart crutch tip 120R may have provided a visual, auditory, or voice notification to urge the patient 112 to put more weight on the injured lower extremity. Conversely, if the peak load from operation 406 had been less than 126 lbs., meaning that not enough weight was on the crutches 110 and too much weight was on the injured lower extremity, the primary smart crutch tip 120R may have provided a visual, auditory, or voice notification to urge the patient 112 to put less weight on the injured lower extremity.

At the conclusion of operation 408 of FIG. 12, the primary smart crutch tip 120R may store usage data pertaining to the patient step for subsequent analysis. The stored data may include the time at which the step was taken and the peak load on the crutches during the step. In some embodiments, the maximum load on each of the two crutches during the step, as show in FIG. 15A at 440 and FIG. 15B at 442, may also be stored. A step counter for the current day (or, more generally, time interval) may also be incremented.

Operations 404, 406, and 408 may thereafter be repeated for each step taken by the patient using the crutches 110. In the result, the primary smart crutch tip 120R may accumulate usage data for multiple steps taken at various times during the patient's rehabilitation program. This usage data is periodically wirelessly transmitted back to the mobile patient app 132, e.g., via Bluetooth™ LE, when connectivity with the mobile device 130 is available. In one embodiment, the usage data is sent in real time immediately after each step is taken.

Figure 17:
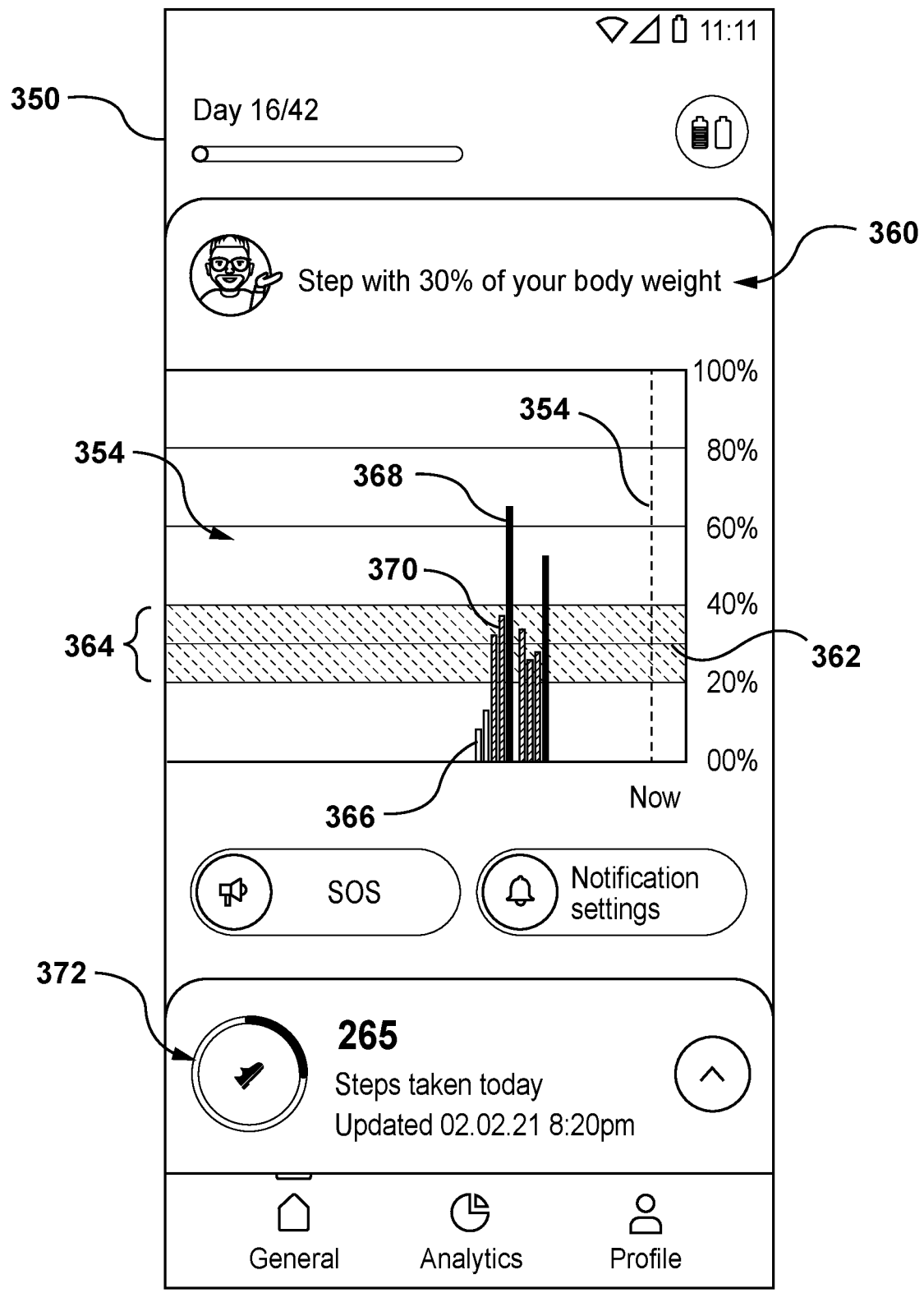
FIG. 17 depicts another GUI displayed by the mobile patient software application at the patient mobile device of FIG. 1.

The mobile patient app 132 may be used to display various types of analytics of the patient's usage of the crutches 110 during the rehabilitation program. For example, referring to FIG. 17, the main GUI 350 of the mobile patient app 132 may display recent usage data in display area 354. In the GUI 350, individual steps are represented as bars in a bar graph whose vertical axis indicates load on the injured lower extremity (expressed in relative terms, e.g., percent) and horizontal axis represents time. The currently operative target load for the injured lower extremity (30% in this example) may be displayed in a textual banner 360 and as a horizontal line 362 in the bar graph. The range of weights that are considered compliant (in this example, from 20% to 40% of body weight) may be indicated, e.g., by highlighting the range using a differently colored graph background 364.

In GUI 300, the bars of the bar graph may be color-coded. Steps with insufficient load on the injured lower extremity may be denoted by a white bar 366; steps with an excessive load on the injured lower extremity may be denoted by a red bar 368; and steps that were compliant with the operative recommended target load may be denoted by a green bar 370. Such color coding, or other types of visual indicators, may provide valuable, at-a-glance user feedback as to whether the crutches 110 are being properly used. A step count indicator 372 may provide a tally of steps taken during the current day and may provide a progress indicator showing progress towards a daily goal, which the doctor may prescribe through the mobile doctor app 142.

The mobile patient app 132 also relays the recent usage data that it continuously or periodically receives from the primary smart crutch tip 120R to the cloud-based backend software application 162 for storage in connection with the database record for patient 112. The stored usage data information is accessible by the mobile doctor app 142 and/or web-based doctor app 152.

Figure 18:
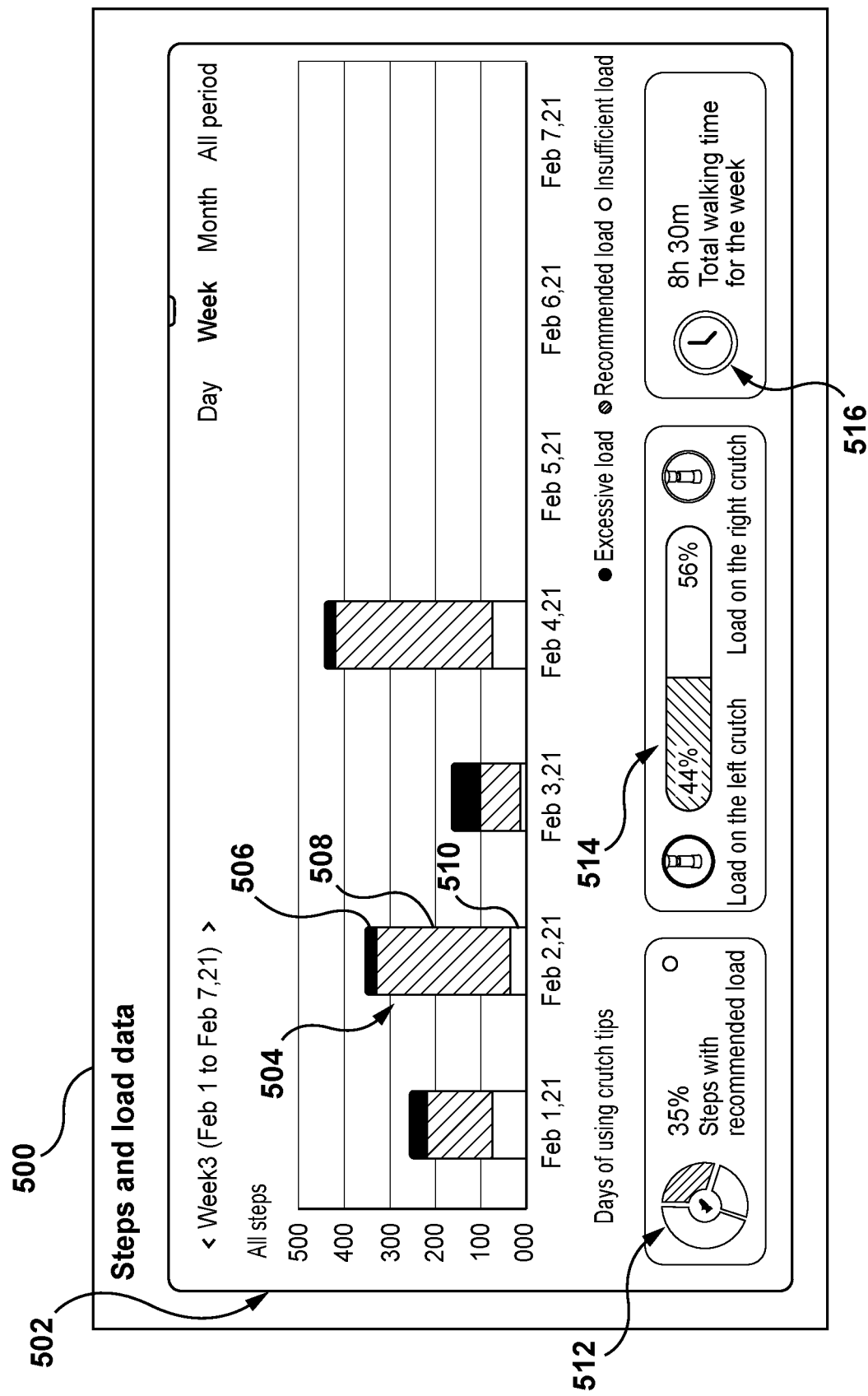
FIG. 18 depicts a GUI displayed by a web-based doctor software application at the doctor mobile device of FIG. 1.

The doctor 116 may use the doctor app 142 or 152 to remotely monitor, in real time or near-real time, the patient's usage of the crutches 110 during the rehabilitation program. Various types of analytics may be viewable. For example, FIG. 18 illustrates an example GUI 500 of the web-based doctor app 152. This GUI 500 can be used to display historical usage data of the patient 112. A similar GUI 500 could be generated and displayed at the mobile patient app 132.

The example GUI 500 includes a composite bar graph 502 in which the vertical axis represents step count and the horizontal axis identifies the day (or, more generally, a chosen time interval) of the rehabilitation period. Each bar represents steps taken using the crutches 110 in a single day. The height of the bar represents total steps taken during the relevant day. The component bar portions making up each bar collectively indicate the proportion of the steps taken during that day in which the load on the injured lower extremity was too high, too low, or in the recommended range.

For example, bar 504 represents steps taken on Feb. 2, 2021. The height of the bar 504 indicates that 350 steps were taken using the crutches 110 on that day. A first bar portion 506 shows that, for 20 of those steps, the load on the injured lower extremity was excessive. A second bar portion 508 shows that, for 300 of those steps, the load on the injured lower extremity was in the recommended range, i.e., compliant with the target load. A third bar portion 510 shows that, for 30 of those steps, the load on the injured lower extremity was insufficient.

A pie chart icon 512, or similar GUI construct, may be used to present an at-a-glance graphical indicator of the proportion of excessively loaded, insufficiently loaded, or compliant steps taken by the patient 112 during a chosen duration of the rehabilitation period (e.g., day, week, month, or total rehabilitation period). Another icon 514 may be used to present an at-a-glance graphical indicator of a proportion of weight being loaded onto the left crutch 110L versus the right crutch 110R, on average, for a chosen duration. The GUI may further display the total time spent walking using the crutches 110 for the currently displayed interval, such as a week.

The doctor can also make changes to the weight-bearing rehabilitation program if necessary. Any such changes are communicated to the patient app and are relayed to the smart crutch tip devices. This may result in an update to the rehabilitation program data 144 array elements corresponding to the current day and any days remaining in the rehabilitation period.

As will be appreciated, the described system 100 provides a flexible and convenient mechanism for a patient 112 and a doctor 116 to monitor for patient compliance with a prescribed lower extremity rehabilitation program, even when the target load dynamically changes. After being configured once at the outset of a rehabilitation period, the smart crutch tips 120 can change the target load autonomously and automatically during the rehabilitation period, in accordance with the rehabilitation program. The smart crutch tips 120 can also monitor for compliance with the dynamically changing target load throughout the rehabilitation program. The likelihood of patient compliance with the rehabilitation program may be improved in comparison to conventional techniques.

As described above, the smart crutch tip 120 has attachment means (nut 212 and resilient split ring 214) for selectively attaching the smart crutch tip 120 to various types of walking aids. The ability to attach the device 120 to different walking aids may be considered advantageous because the same device can be used for rehabilitation from different types of lower extremity injuries.

Nevertheless, the attachment means may contribute to device complexity, weight, and production cost. Moreover, attachment of the smart crutch tip 120 to a walking aid may increase the height of the walking aid by perhaps 8 to 12 centimeters in some embodiments, which may make the walking aid too tall for a patient to use properly. For this reason, it may be necessary to reduce the height of the walking aid by a complementary amount, e.g., by collapsing a telescoping leg portion of the walking aid, when the smart crutch tip 120 is attached. Some patients may consider attaching the smart crutch tip 120 and adjusting the walking aid height to be tedious. Moreover, some patients may consider the added weight and/or girth of the smart crutch tip 120 device(s) to feel awkward, at least initially, as compared with using the walking aid by itself.

For such patients, a different embodiment of electronic device, which is similar to smart crutch tip 120 in terms of functionality but lighter and integrally formed with, or embedded within, the walking aid, may be preferred. One such example embedded smart crutch tip device is depicted in FIGS. 19, 20, and 21.

Figure 19:
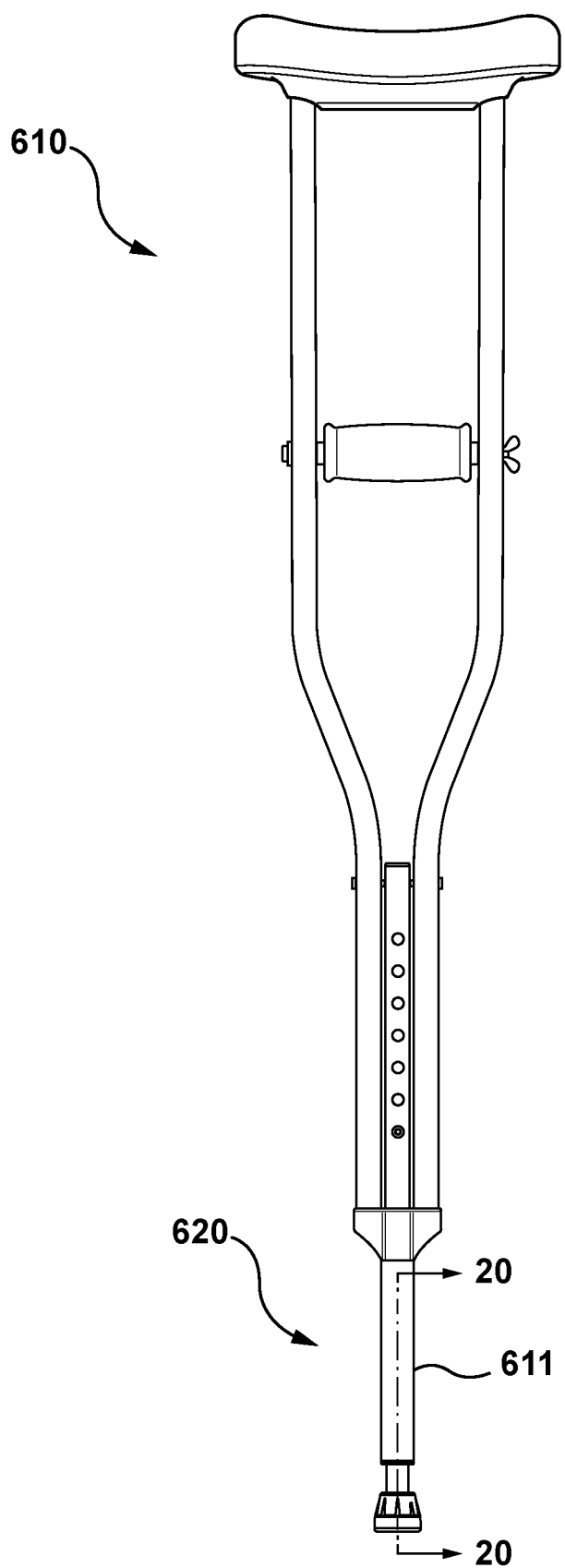
FIG. 19 is an elevation view of an alternative embodiment of the smart crutch tip electronic device that is integrally formed with a crutch.

FIG. 19 is an elevation view of an axillary crutch 610 (a form of walking aid) having a smart crutch tip 620 integrally formed therewith. The smart crutch tip 620 is an electronic device whose functionality is like that of smart crutch tip 120. The form factor of the crutch 610 depicted in FIG. 19 is such that, from outward appearances, the presence of an embedded smart crutch tip 620 is not immediately apparent. This is not strictly required but may facilitate patient acceptance of smart crutch tip technology.

The electronics of smart crutch tip 620 are arranged to fit within the body or structure of the walking aid. In the depicted embodiment, the smart crutch tip 620 is designed to fit within a tubular leg portion 611 of the crutch 610. The crutch leg 611 (or, more generally, walking aid body) acts as the housing for the smart crutch tip 620, reducing or eliminating the need for a dedicated housing, such as housing 202 of smart crutch tip 120 (see, e.g., FIG. 5). This may help to reduce a weight and/or bulkiness of the smart cane tip 620.

Figure 20:
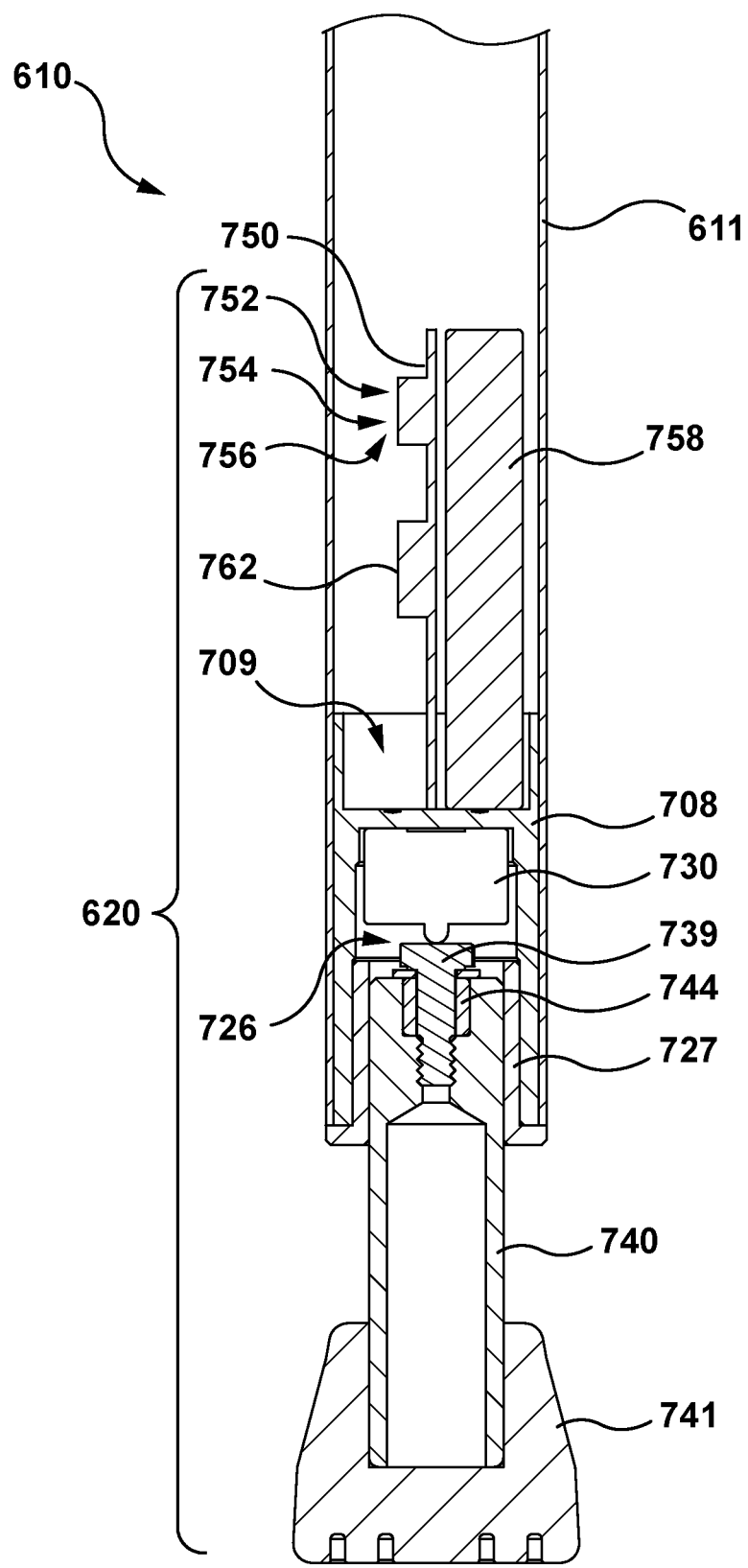
FIG. 20 is a cross-section of the smart crutch tip electronic device of FIG. 19 taken along line 20-20.
Figure 21:
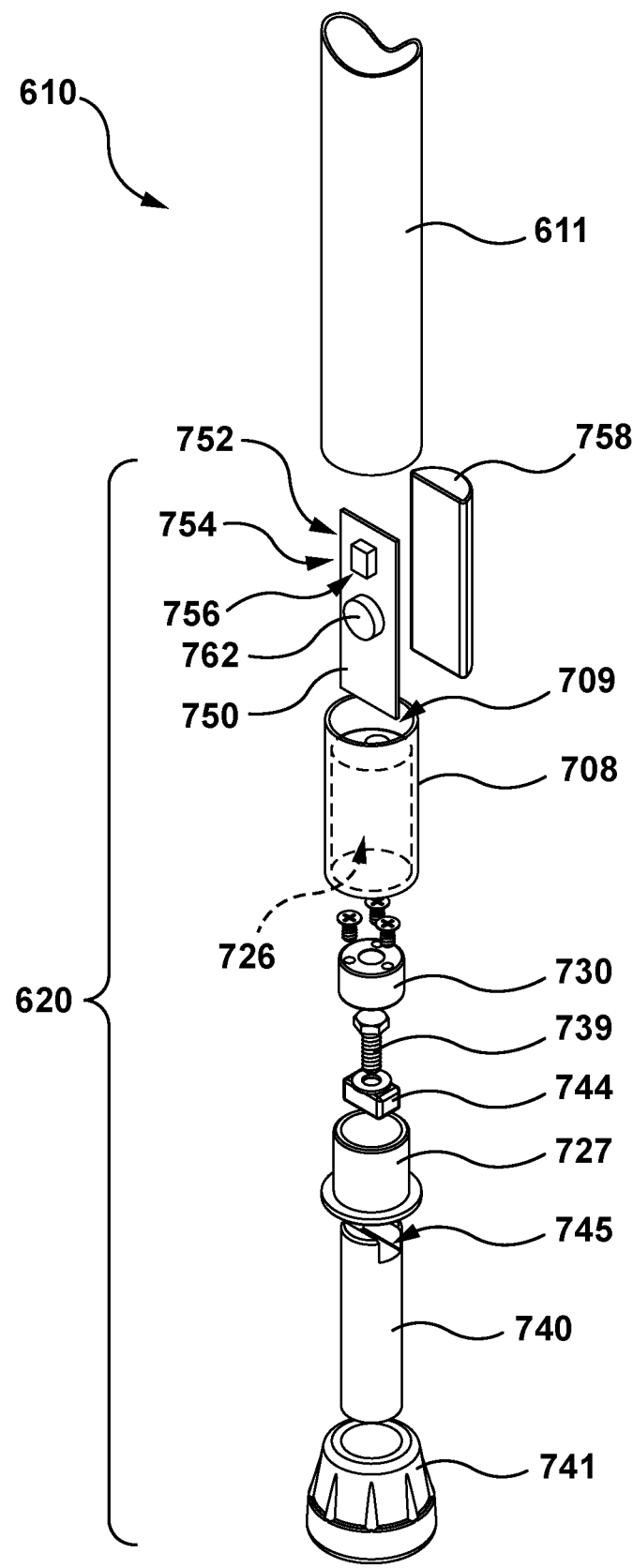
FIG. 21 is an exploded view of the smart crutch tip device of FIG. 19.

FIG. 20 is a cross-section of the embedded smart crutch tip 620 taken along line 20-20 of FIG. 19. FIG. 21 is an exploded view of the smart crutch tip 120 with some components (e.g., fasteners) omitted and other components (e.g., circuitry) depicted schematically for clarity.

Referring to FIGS. 20 and 21, it should be appreciated that many components of the smart cane tip 620 are analogous to counterpart components in smart crutch tip 120 of FIGS. 5 and 6. These components include the processor 752, memory 754, and short-range wireless transceiver 756 (e.g., Bluetooth™ transceiver), which may be analogous to processor 252, memory 254, and transceiver 256 described above, and may all form part of a Bluetooth™ 5 module or Bluetooth™ BLE module. The auditory notification element 762 is also analogous to auditory notification element 262, shown above.

In the present embodiment, the above-referenced electronic components are mounted to a surface of a printed circuit board 750 having an elongate shape designed to fit inside the hollow crutch leg 611. A battery 758 for powering the smart crutch tip 120 electronics may have a semi-cylindrical shape (see, e.g., FIG. 21) to maximize utilization of space between the opposite side of the printed circuit board 750 and the wall of crutch leg 611.

The example smart crutch tip 620 has a generally tubular body 708, fixed with respect to the crutch leg 611, that acts as a primary structural element for the device. The body 708 of this embodiment is differently shaped from body 208 described above. In particular, the body 708 has a shallow top receptacle 709 with an open top and a deeper bottom receptacle 726 with an open bottom. The top receptacle 709 supports the printed circuit board 750 and battery 758. The deepest (uppermost in FIGS. 20 and 21) portion of the bottom receptacle 726 accommodates a load sensor 730.

A tubular flanged collar 727 fits snugly within the bottom receptacle 726, below the load sensor 730. The collar 727 has a cylindrical central opening that is sized to slidably receive a crutch tip base 740. The base 740, which is a cylindrical post in the present embodiment, is configured for limited axial movement (translation) with respect to the collar 727 and body 708 of the smart crutch tip 120 (vertically in FIGS. 20 and 21). The base 740 has a rubber foot 741 at its lower end.

As perhaps best seen in FIG. 20, the smart crutch tip 620 includes a base stop 744 that limits downward movement of the base 740 relative to the body 708 of the smart crutch tip 620. As with the base stop 244 of the earlier-described embodiment, the base stop 744 of the present embodiment is a cuboid rigid element held within a notch 745 at the upper end of the base 740 by a bolt 739. Other forms of base stop could be used in alternative embodiments.

The load sensor 730 is disposed between the body 708 and the bolt 739 (and thus base 740, of which bolt 739 may be considered as a part). As such, the load sensor 730 is in the load path of the smart crutch tip 620.

Configuration and operation of the smart crutch tip 620 may be performed as described above for smart crutch tip 120 and as shown in FIGS. 8-14, 15A, 15B, and 16-18, with certain exceptions. Once such exception is that the patient 112 need not attach any device(s) to his or her walking aid, since the smart crutch tip 620 is already integral therewith. Another exception is that user notifications directly from the smart crutch tip 620 may be limited to auditory user notifications rather than visual ones, because the illustrated embodiment lacks a visual user notification indicator (although one could be provided in alternative embedded crutch tip embodiments). Otherwise, operation of the mobile patient app 132, the mobile doctor app 142, and the web-based doctor app 152 may be the same as the operation of these apps that was described above for removable smart crutch tips 120.

As with smart crutch tips 120R and 120L, in cases when a pair of smart crutch tips 620R, 620L are used as a pair, one of the smart crutch tips 620R is predesignated as the primary device, and the other smart crutch tip 620L is predesignated as the secondary device. Intercommunication between the primary and secondary smart crutch tips 620R and 620L may occur as described above for devices 120R and 120L. Each smart crutch tip 620R, 620L may be considered to be associated with the crutches 110R, 110L, respectively, with which they are integrally formed.

Figure 22:
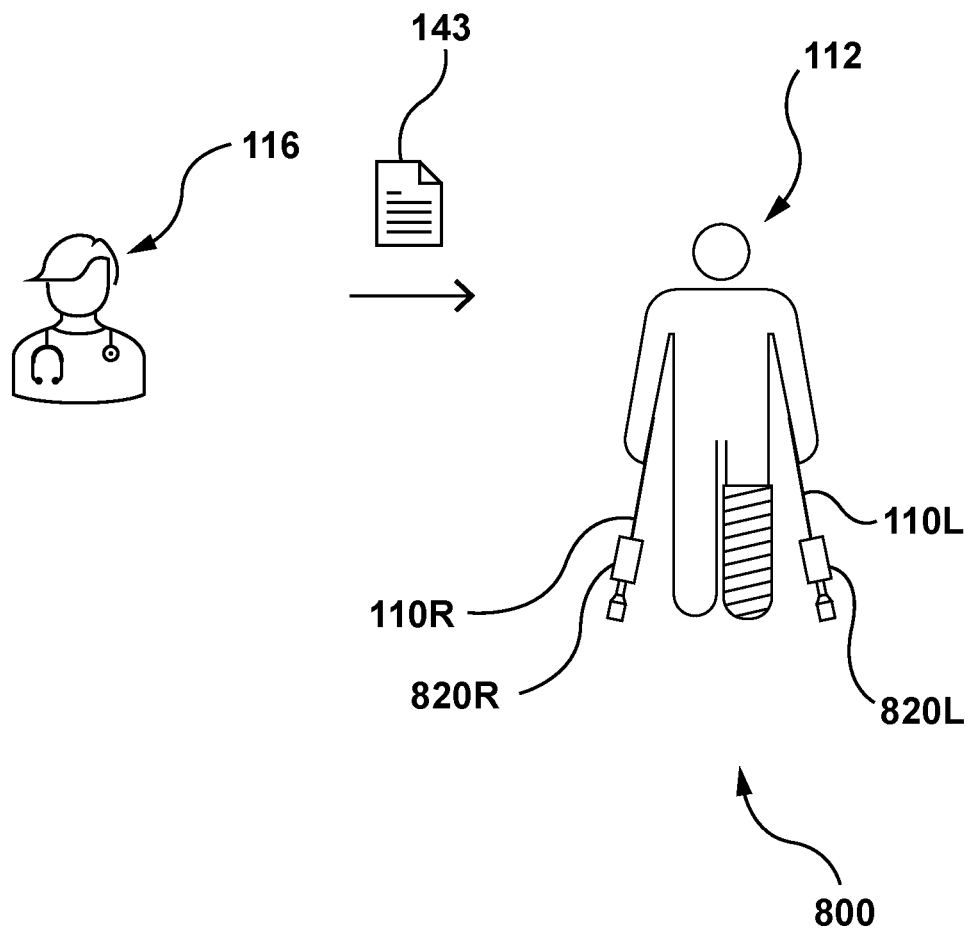
FIG. 22 is a schematic diagram of an alternative embodiment system for promoting proper use of a during lower extremity rehabilitation.

FIG. 22 illustrates an example alternative system 800 for encouraging proper use of a walking aid (e.g., a pair of crutches 110) during lower extremity injury rehabilitation. Like system 100, described above, system 800 includes a pair of smart crutch tips 820R, 820L (generically or collectively smart crutch tip(s) 820). Each of the smart crutch tips 820 is an electronic device that is similar in many respects to smart crutch tip 120. For example, each smart crutch tip 820 is attachable to a respective one of crutches 110 to dynamically measure the load placed on the crutch 110 as it is being used. Moreover, the smart crutch tips 820R, 820L are designed to intercommunicate wirelessly to amalgamate dynamic load information from the two crutches 110, as described above in connection with FIG. 14 for crutch tips 120R, 120L.

Yet, each smart crutch tip 820 differs from the smart crutch tip 120 in certain respects. A key difference is that the smart crutch tip 820 incorporates a display component and user input mechanism (UIM) not present in smart crutch tip 120. The display and UIM are usable by the patient 112, as will be described, to manually program the device consistently with a rehabilitation program from a doctor 116. Another difference is that, for simplicity, smart crutch tip 820 does not store, or relay to any other device, historical usage data showing how the walking aid has been used during the current rehabilitation period (e.g., as graphically represented in GUI 500 of FIG. 18 for example). Rather, smart crutch tip 820 is limited to providing immediate feedback to the patient 112, in real time, in the form of one or more user notifications, e.g., visual indicators, auditory indicators, or voice indicators. These user notifications may be similar to those provided by smart crutch tip 120, e.g., notifying the patient 112 whenever the weight applied to the walking aid is excessive or insufficient.

These differences between smart crutch tip 820 and smart crutch tip 120 permit the system 800 to be greatly simplified in comparison to system 100 of FIG. 1. For example, the example system 800 omits the following components of system 100 (see FIG. 1): the mobile patient app 132 executed at a patient mobile device 130; the mobile doctor app 142 and/or web-based doctor app 152 being executed at a doctor mobile device 140 and computer 150, respectively; and backend server application 162 executed at the cloud-based server 160. The cost of implementing and maintaining the system 800 may accordingly be reduced compared to system 100.

System 800 may be considered particularly suitable for patient rehabilitation in certain patient and/or doctor scenarios, e.g.: when the doctor 116 lacks access to, or is unwilling to use, the mobile doctor app 142 or web-based doctor app 152; when the patient 112 lacks a suitable mobile device for executing the mobile patient app 132; when the patient 112 is in a remote location with no internet connectivity, which may prevent the patient-specific rehabilitation program parameter data 143 originating from doctor app 142 or 152 from being transmitted to a mobile patient app 132 and being converted to patient-specific rehabilitation program data 144 and wirelessly transmitted to smart crutch tip 120; when the patient 112 prefers to have manual control over rehabilitation program parameters; or a combination of these factors.

A possible trade-off of using system 800 rather than system 100 may be a greater responsibility upon the patient 122 for correctly setting his or her own rehabilitation program parameter settings, including target load and time interval (duration), as described below. In view of this responsibility, system 800 may be best suited for more straightforward rehabilitation programs, e.g., ones with constant target load settings over extended periods of time, than for complicated rehabilitation programs with frequently changing target loads upon the walking aid.

Figure 23:
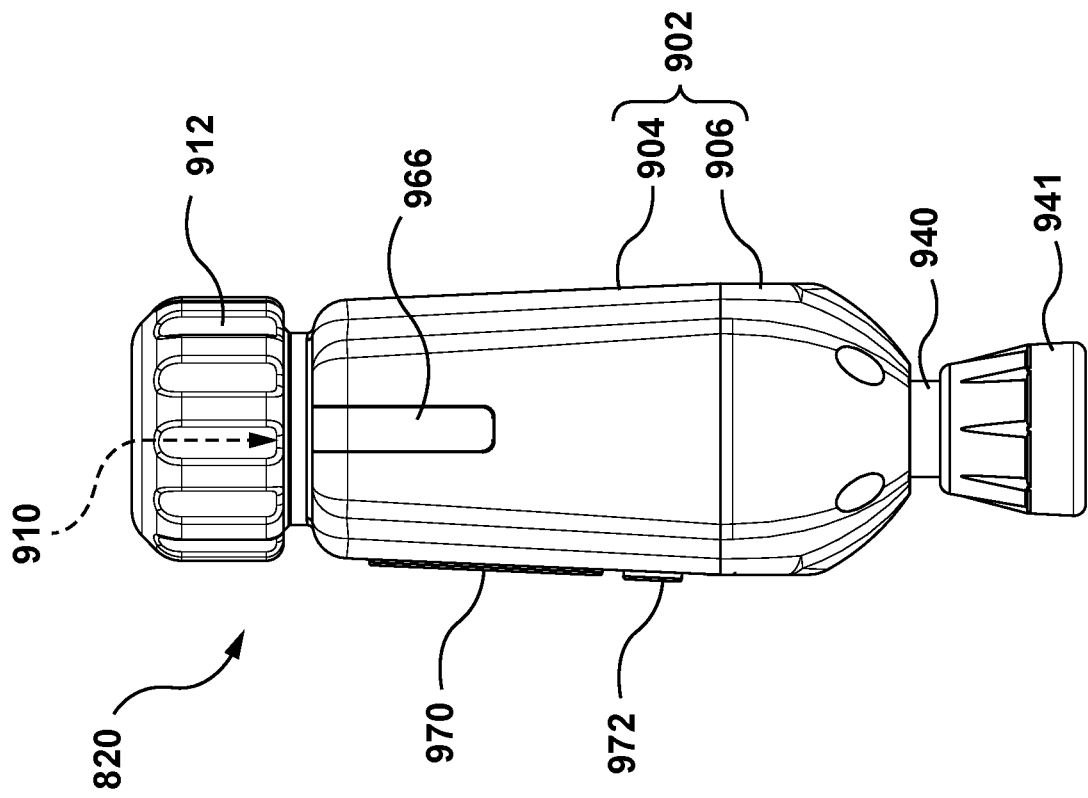
FIG. 23 is a front elevation view of one of the smart crutch tip electronic devices of FIG. 22.
Figure 24:
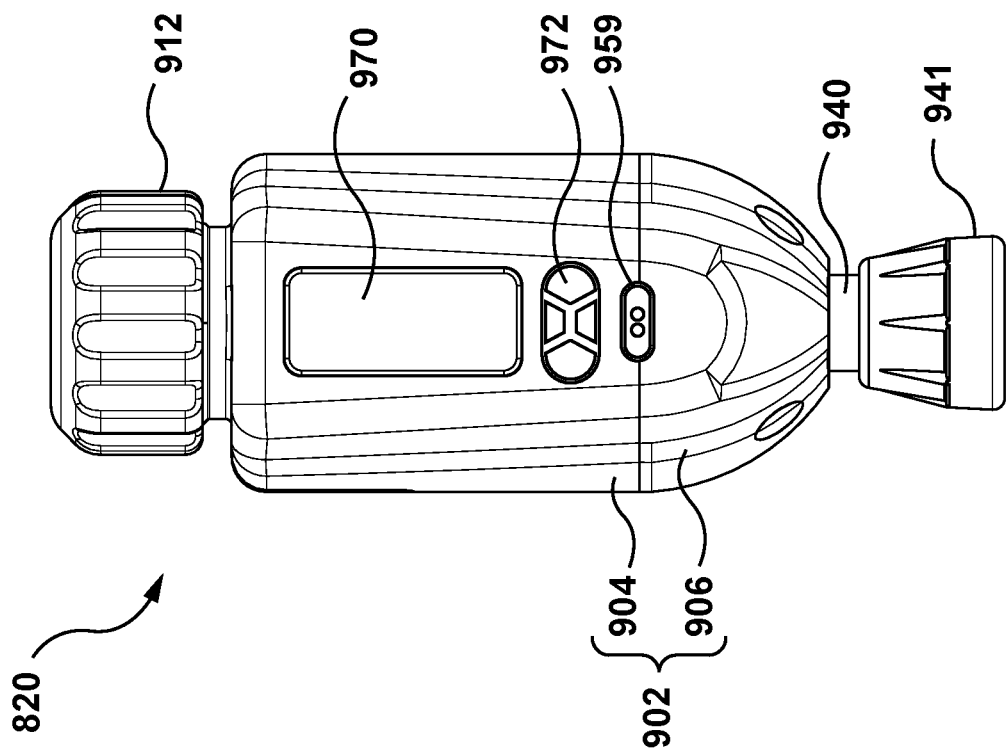
FIG. 24 is a side elevation view of the smart crutch tip electronic device of FIG. 23.
Figure 25:
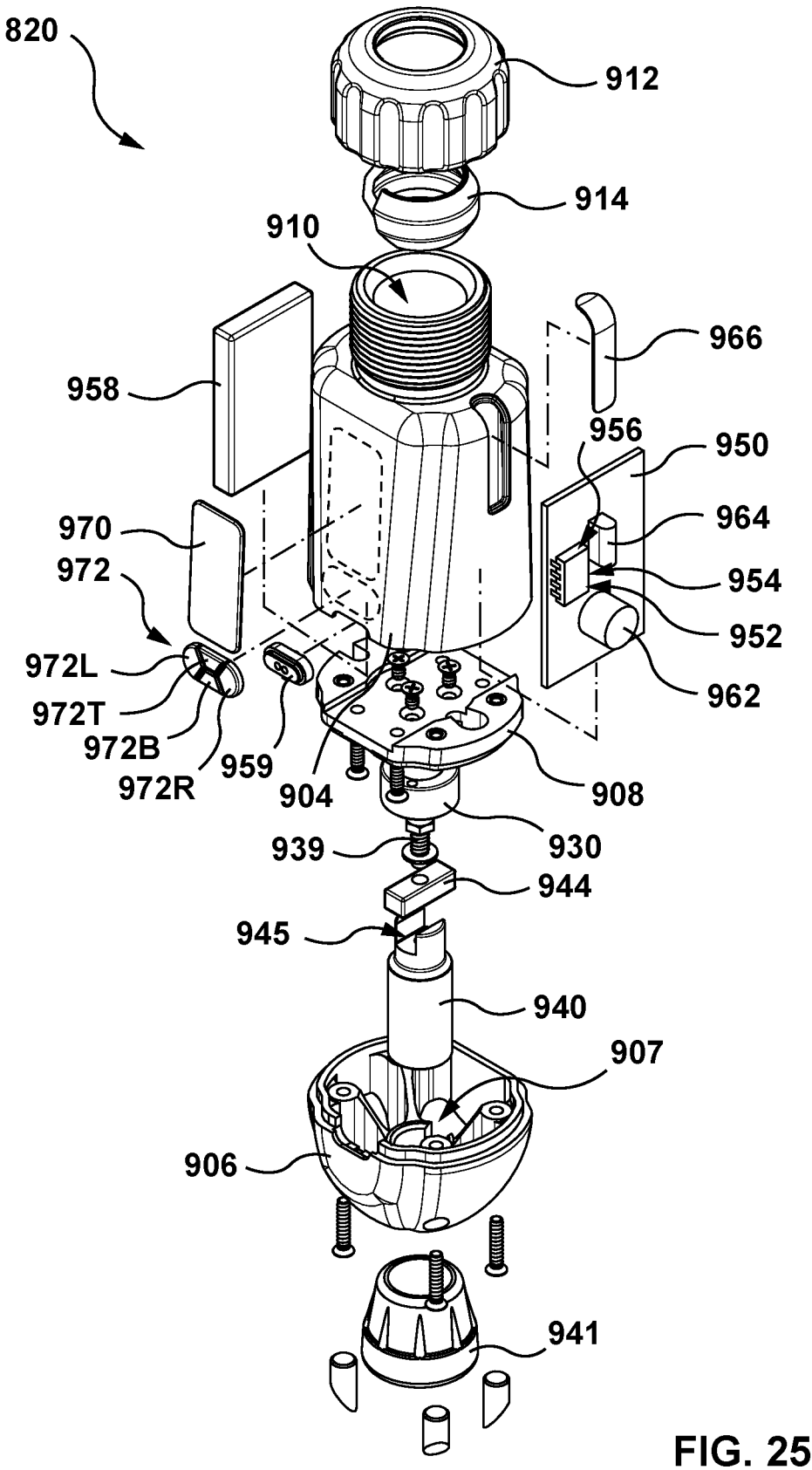
FIG. 25 is an exploded view of the smart crutch tip electronic device of FIG. 23.

FIGS. 23 and 24 are front and side elevation views, respectively, of an example embodiment of a smart crutch tip electronic device 820 of system 800. FIG. 25 is an exploded view of the smart crutch tip 820 in which some components are depicted schematically or are omitted for clarity.

Like smart crutch tip 120, described above, the example smart crutch tip 820 has a housing 902 comprised of an upper housing portion 904 and a lower housing portion 906, to facilitate device assembly. The housing 902 may have different shapes and/or different components in alternative embodiments.

The smart crutch tip 820 has a receptacle 910 that is sized and shaped for receiving the tip of a leg of a walking aid, such as a crutch tip, from above. A nut 912 and a resilient split ring 914 (see FIG. 25) at the open end of the receptacle comprise attachment means for selectively attaching the smart crutch tip 820 to the walking aid, as described above.

The housing portion 904 attaches to a flat body element 908. The two components collectively define a cavity in which the receptacle 910 is formed and electronics are housed. The housed electronics include a processor 952, memory 954, and short-range wireless transceiver 956, all communicatively coupled with one another and mounted to a printed circuit board 950. The processor, memory, and transceiver may for example comprise a Bluetooth™ 5 module or Bluetooth™ BLE module, which may be a single integrated circuit. The memory 954 includes processor-executable instructions, e.g., firmware, that govern operation of the smart crutch tip 820 as described herein. The instructions may for example be loaded during manufacture of the smart crutch tip 820 and may be subsequently updated, e.g., via flashing. A battery 958 powers the electronics of smart crutch tip 820 and is rechargeable via a charging port 959.

An auditory notification element 962 (e.g., a buzzer) and a visual notification element 964 (e.g., an LED) are also mounted to the printed circuit board 950 and are controllable by the processor 252. A transparent cover 966 protects the visual notification element 964.

As alluded to above, the smart crutch tip 820 further includes a display 970 and user input mechanism 972. The display may for example by a liquid-crystal display (LCD) screen. In the present embodiment, the UIM 972 comprises four physical buttons 972R, 972L, 972T, and 972B. The display 970 and UIM 972 may be mounted to the upper housing portion 904, e.g., by surface mounting or in corresponding openings that are sized and shaped to receive these components, and are communicatively coupled to processor 952.

The lower housing portion 906 has a central opening 907 that slidably receives a cylindrical post or base 940 with a rubber foot 941 at its lower end. A base stop 944, similar to base stops 244 and 744 described above, limits downward axial translation of the base 940 relative to the body 908 and housing 902 of the smart crutch tip 820. The base stop 944 fits within a notch 945 at the upper end of base 940 and is attached to base 940, e.g., using a bolt 939.

A load sensor 930 is disposed between the body portion 908 and the bolt 939 (and thus base 740, of which bolt 739 may be considered as a part). As such, the load sensor 930 is in the load path of the smart crutch tip 820.

The smart crutch tips 820R and 820L may be predesignated as primary and secondary, respectively, as described above for smart crutch tips 120R and 120L. When the primary smart crutch tip 820R is activated, it may automatically establish a wireless connection with the secondary smart crutch tip 820L. This may be done via a short-range wireless communication mechanism such as Bluetooth™ using a preprogrammed MAC address, as described above.

Unlike smart crutch tips 120R and 620R, described above, the primary smart crutch tip 820R of the present embodiment is not operable to wirelessly receive patient-specific rehabilitation program data 144 originating from the doctor 116 defining one or more time intervals with target load specified for each time interval (e.g., as depicted in FIG. 10). Rather, smart crutch tip 820R is manually programmable by a user, such as patient 112, to specify rehabilitation program parameters for only a single time interval at a time. The rehabilitation program parameters 143 may be specified by a doctor 166, during an in-person visit or over the phone for example (see FIG. 22). The parameters 143 may include multiple time intervals with different targets loads for different intervals.

Figure 26:
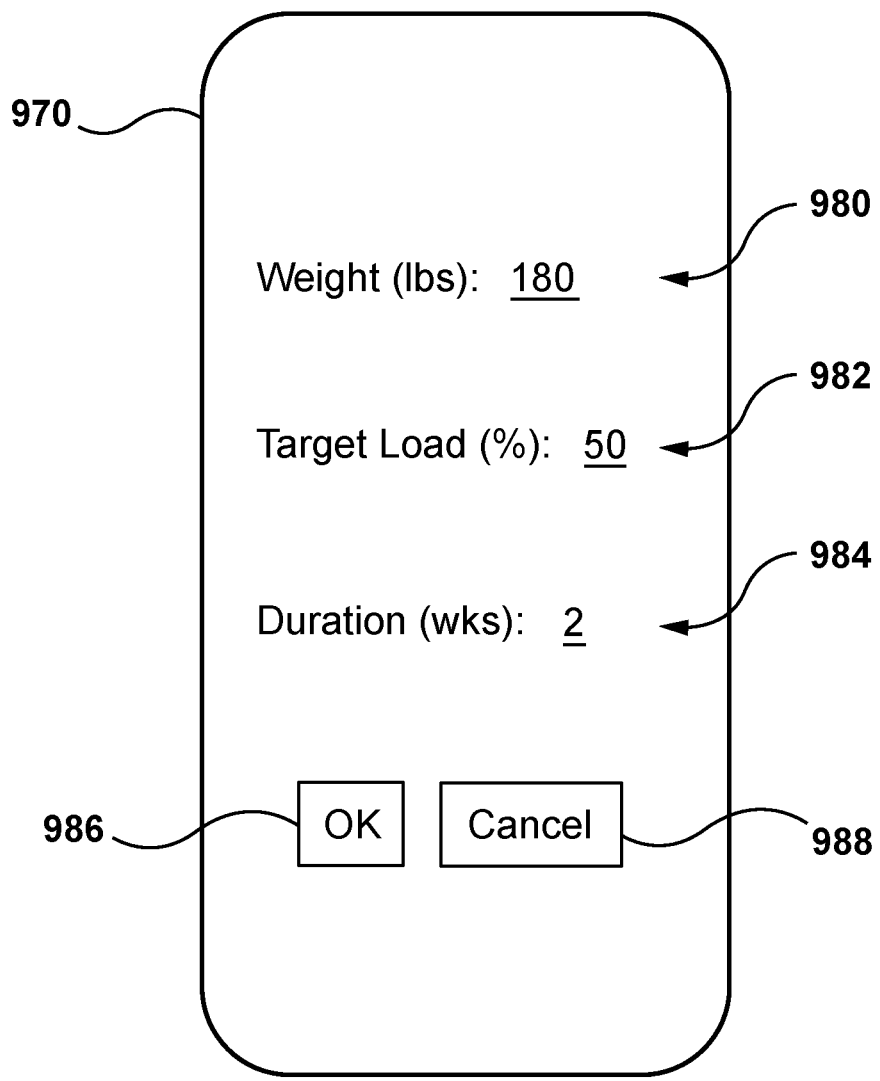
FIG. 26 shows a user interface for configuring the smart crutch tip electronic device of FIG. 23.

To effect manual programming (configuration) of the smart crutch tip 820, firmware stored in memory 954, when executed by processor 952, may cause the display 970 to present three textual fields, as shown in FIG. 26, representing user-configurable rehabilitation program parameters for a single time interval of a rehabilitation program. In this example, the first field 980 is for specifying the body weight of the patient, e.g., in pounds. The second field 982 is for specifying the target load on the injured lower extremity relative to the body weight, e.g., as a percentage value from 0% to 95%. The third field 984 is for specifying a duration of a single time interval, e.g., in weeks.

In one embodiment, a user may be able to configure the values in these fields as follows. User selection of the right button 972R or left button 972L, respectively, of the UIM 972 (see FIG. 25) may cause a cursor (e.g., reverse video highlighting) to tab forward or backward through the fields 980, 982, and 984. When the cursor highlights a particular field 980, 982, or 984, user selection of the top button 972T or bottom button 972B, respectively, may cause the value of that field to increase or decrease by some predetermined increment (e.g., in field 980, by 5-pound increments). When the values in fields 980, 982, and 984 are set as desired, the cursor may be tabbed to either of the "OK" user input construct 986 or "Cancel" user input construct 988, e.g., using buttons 972R or 972L. Then, selection of one of the top button 972T or bottom button 972B may cause any changes made to the values in any of fields 980, 982, and 984 to be accepted or rejected.

When the values in the fields 980, 982, and 984 are accepted, the processor 952 may automatically compute the target absolute load on the walking aid for the specified time interval based on the patient weight specified in FIG. 980 and the target relative load on the injured lower extremity specified in FIG. 982. For example, if the patient weight specified in field 980 is 200 pounds and the target relative load on the injured lower extremity specified in field 982 is 40%, then the target absolute load on the walking aid may be computed by calculating the absolute load on the injured lower extremity and subtracting that absolute load from the body weight, as follows: 200 pounds—(200 pounds*40%) =120 pounds.

After some predetermined number of steps has been taken with the walking aid 110 (e.g., five steps), the time interval of the rehabilitation program, as specified in FIG. 984 of FIG. 26, may be considered to have commenced. The processor 952 may initiate a countdown timer that has been set to the time interval duration.

Operation 400 of the primary smart crutch tip 820R for monitoring compliance with the currently operative target load, as computed from the values of fields 980 and 982 (see above), is depicted in FIG. 12. Operation 400 may be triggered whenever motion is detected at the smart crutch tip 820R, e.g., using an accelerometer (not expressly depicted).

In operation 402, a currently operative time interval of the at least one time interval of the rehabilitation period is identified. In the present embodiment, the currently operative time interval is the one whose duration was specified in field 984 of FIG. 26. Operation 402 may entail verifying that the time interval remains unexpired, e.g., by confirming that the countdown timer has not yet expired.

In operation 404 (FIG. 12), data is received from one or more load sensors indicative of a dynamic load on the walking aid during a patient step. For the present scenario, in which the walking aid comprises multiple units (two crutches 110), operation 404 may entail the steps shown in FIG. 13, as described above.

In operation 406 (FIG. 12), the primary smart crutch tip 820R determines, based upon the received data, a peak load upon the pair of crutches 110 collectively during the patient step. For the present scenario, in which the walking aid comprises two crutches 110, operation 406 may entail the steps depicted in FIG. 14, described above.

In operation 408 (FIG. 12), a user notification is provided indicating whether the peak load upon the walking aid during the patient step, as determined in operation 406, is non-compliant with the target load for the currently operative time interval. In the present embodiment, the patient 112 is considered to have complied with the target load if the peak load is within a range that is centered on the current target load and whose limits are a predetermined percentage (e.g., 10%) greater than and less than the target load. The primary smart crutch tip 820R may for example provide a visual, auditory, or voice notification to urge the patient 112 to put more weight or less weight on the injured lower extremity when the target load on the walking aid is found to be excessive or insufficient, respectively.

Operations 404, 406, and 408 may thereafter be repeated for each step taken by the patient using the crutches 110. In the present embodiment, the primary smart crutch tip 820R does not store usage data for multiple steps taken at various times during the time interval, nor is in this information periodically communicated to any mobile patient app at a patient mobile device.

When the time interval expires (e.g., upon expiry of the countdown timer), then the processor 952 may trigger an audible or visual user notification indicative of that. The processor 952 may, alternatively or in conjunction, cause a prompt to be displayed on display 970 for entry of further user input via the user input mechanism 972. The prompt may seek user input of a new target relative load on the injured lower extremity and a new time interval of the rehabilitation period during which the new target load on the walking aid is to be operative, e.g., via fields 982 and 984 described above. Once these new parameters have been entered and accepted, the processor 952 may automatically recompute the target absolute load on the walking aid for the specified time interval based on the earlier-specified patient weight and the newly specified target relative load. Thereafter, operation 400 may be repeated with the new target absolute load and for the newly specified time interval. This may be repeated as many times as necessary for a given rehabilitation period.

It will be appreciated that, although the electronic devices 120, 620, and 820 are referred to above as a smart "crutch tips", the devices are not necessarily used only with crutches. They could alternatively be installed onto, or be integrally formed with, other types of walking aids, such as canes.

All references to a "doctor" in this document should be interpreted as being inclusive of any other medical professional who may be qualified to prescribed and monitor patient progress through a lower extremity rehabilitation program, such as a physical therapist for example. Similarly, all references to a "patient" in this document should be interpreted as inclusive of any users of a walking aid as described herein, regardless of whether the users are formally under the care of a medical professional at the time of use.

It will be appreciated that each memory 254, 754, and 954 described herein constitutes a form of non-transitory, machine-readable medium, other forms of which may include magnetic or optical storage media.

Various alternative embodiments are possible.

As noted above, it is possible to use a smart crutch tip device 120, 620, or 820 to monitor for patient compliance with a rehabilitation program when the walking aid comprises only one unit, such as a single crutch, rather than a pair. In this case, there would be no secondary smart crutch tip. In the case of smart crutch tip 120 or 820, the sole device would be installed onto the leg of the sole walking aid unit, as described above, or in the case of smart crutch tip 620 would be integrally formed therewith. The sole devices 120, 620, and 820 would not receive wireless signals from any secondary smart crutch tip. In the case of devices 120 and 620, wireless communication with the patient mobile device 130 would still occur.

In such a single-device scenario, operation 400 of the primary (and sole) smart crutch tip 120, 620, or 820 would still be as described above in FIG. 12, with the following exceptions. Operations 404 and 406 would not be performed according to the steps outlined in FIGS. 13 and 14 respectively. Rather, operation 404 of FIG. 12 may entail only step 410 of FIG. 13, with step 412 being unnecessary. Moreover, referring to FIG. 14, performing operations 420 and 422 would be unnecessary, and step 424 would entail determining the peak load based solely on the dynamic load as measured by the primary smart crutch tip 120R, 620R, or 820R during the patient step.

The above-described embodiments use a short-range wireless communication technology, such as Bluetooth™, for transmitting dynamic load information from the secondary smart crutch tip 120L, 620L, or 820L to the primary smart crutch tip 120R, 620R, or 820R, respectively, in real time. A short-range wireless communication technology (be it Bluetooth™ or some other technology) may be used because the expected distance between the paired primary and secondary smart crutch tips during use is expected to be well within the short-range communication limit of about 10 meters.

The above-described embodiments further use a short-range wireless communication technology, such as Bluetooth™, for communicating the collective dynamic load on the pair of crutches 110 from the primary smart crutch tip 120R or 620R to the mobile device 130 in real time. It is possible that the distance between the mobile device 130 and the primary smart crutch tip 120R or 620R could exceed a maximum range, e.g., if the mobile device 130 were left in another room from the smart crutch tips. In that case, wireless communication between the primary smart crutch tip 120R or 620R and the mobile device 130 may be interrupted. Until communication can be reestablished, the primary smart crutch tip 120R or 620R may buffer, e.g., in flash memory, collective load information for each step taken from the time at which communication was interrupted. It is for this reason (at least in part) that a capacity of memory at the primary smart crutch tip 120R or 620R may be larger than memory capacity at the secondary smart crutch tip 120L or 620L, respectively.

It is possible that a longer-range wireless communication technology (e.g., a medium or long-range technology) could be used for communication between the primary smart crutch tip 120R or 620R and the mobile device 130 or possibly even for communication between the secondary smart crutch tip 120L, 620L, or 820L and the primary smart crutch tip 120R, 620R, or 820R, respectively. Longer range wireless communication technology may reduce a risk of any loss of communication between the devices, e.g., if real time user notification of load upon crutches 110 is crucial for some reason. A tradeoff may be higher cost of manufacture for smart crutch tips employing such longer-range communication technologies.

Whatever wireless communication technology is used between these devices (be it short-range or otherwise) should avoid excessive lag. Lag may be considered excessive, e.g., if it prevents any requisite user notification regarding load on the crutches 110 for the most recent step from being provided at the primary smart crutch tip 120R before a subsequent step is taken. References to "real time" user notification in this document may include near real-time ("near time") user notification, although any lag in user notification should not be so excessive as to cause confusion over which patient step has triggered the user notification.

In the foregoing description, when a pair of smart crutch tips 120, 620, or 820 is used together, one of the devices is designated as primary device and the other is designated as the secondary device. For clarity, it is not required for the primary device to always be used on the right side of the body of the patient and the secondary device on the left side of the body. The positions of primary smart crutch tip and secondary smart crutch tip relative to the body of the patient could be reversed. Moreover, the position of the primary smart crutch tip relative to the injured lower extremity is immaterial.

In the description of system 100 above, the mobile patient app 132 at the patient mobile device 130 is operable to receive rehabilitation program parameter data originating from doctor 116, the rehabilitation program parameter data including, for each of a plurality of time intervals spanning a rehabilitation period, a target relative load for an injured lower extremity during the time interval relative to patient body weight. The mobile patient app 132 also receives an indication of the patient body weight, e.g., directly from the patient 112 using the mobile patient app 132. This information is used to generate rehabilitation program data 144 comprising a schedule for use by the electronic device associated with the walking aid. The schedule specifies the plurality of time intervals (e.g., days) spanning the rehabilitation period and, for each of the time intervals, a target absolute load for the walking aid during the time interval. This rehabilitation program data 144 is output to the smart crutch tip 120, which uses it to automatically adjust a currently operative target absolute load on the walking aid over time according to the schedule.

It will be appreciated that the operations described in the preceding paragraph need not necessarily be performed at the patient mobile device 130 in all embodiments. For example, in some embodiments, these operations could be performed at another computing device, such as the cloud-based server 160, the mobile doctor app 142, or the mobile doctor app 152.

Other modifications may be made within the scope of the following claims.

What is claimed is:

1. An electronic device for promoting proper use of a walking aid during patient rehabilitation from a lower extremity injury, the device comprising:
    a body having a receptacle configured to receive a tip of a leg of the walking aid;
    a substantially cylindrical housing configured to cooperate with the body to define an enclosed annular space;
    at least one load sensor anchored to the body, the at least one load sensor being configured to measure a load on the walking aid;
    a memory that, during device operation, stores rehabilitation program data defining:
        at least one time interval of a rehabilitation period; and
        for each of the at least one time interval, a target load for the walking aid during the time interval;
    a processor, communicatively coupled to the memory and to the at least one load sensor, operable to:
        identify a currently operative time interval of the at least one time interval of the rehabilitation period;
        receive, from the at least one load sensor, data indicative of a dynamic load on the walking aid during a patient step;
        determine, based upon the received data, a peak load upon the walking aid during the patient step; and
        provide a user notification indicating that the peak load upon the walking aid during the patient step is non-compliant with the target load for the walking aid for the currently operative time interval,
    wherein the memory and the processor are housed within the enclosed annular space;
    a retaining mechanism for retaining the tip of the leg of the walking aid within the receptacle;
    a base configured for limited axial movement relative to the body; and
    a foot at a lower end of the base,
    wherein the at least one load sensor is disposed between the base and the body and is configured to bear a load placed upon the walking aid during use of the walking aid.

2. The electronic device of claim 1 wherein the walking aid is a pair of crutches or canes, wherein the electronic device is a first electronic device associated with a first crutch or cane of the pair, wherein the data from the at least one load sensor is indicative of a dynamic load on the first crutch or cane during the patient step, and further comprising:
    a wireless transceiver configured to receive, from a second electronic device associated with a second crutch or cane of the pair, wireless signals carrying data indicative of a dynamic load on the second crutch or cane during the patient step; and
    wherein the determining of the peak load upon the walking aid during the patient step comprises:
        generating, based on the data indicative of the dynamic load on the first crutch or cane and the data indicative of the dynamic load on the second crutch or cane, a representation of a dynamic load on the pair of crutches or canes collectively during the patient step; and
        based on the generated representation, determining a maximum load on the pair of crutches or canes during the patient step,
    wherein the peak load upon the walking aid during the patient step is the maximum load on the pair of crutches or canes during the patient step.

3. The electronic device of claim 2 wherein the data indicative of the dynamic load on the first crutch or cane includes first timestamp information, wherein the data indicative of the dynamic load on the second crutch or cane includes second timestamp information, and wherein the generating of the representation of the collective dynamic load on the pair of crutches during the patient step comprises;
    using the first timestamp information and the second timestamp information, time-aligning the data indicative of the dynamic load on the second crutch or cane with the data indicative of the dynamic load on the first crutch or cane; and
    summing the data indicative of the dynamic load on the first crutch or cane with the time-aligned data indicative of the dynamic load on the second crutch or cane.

4. The electronic device of claim 1 wherein the receptacle is threaded and wherein the retaining mechanism comprises:
    a threaded nut; and
    a split ring made from a resilient material;
    the nut and the split ring being configured so that, when the tip of the leg of the walking aid is passed through both of the nut and the split ring and is received within the receptacle, threading of the nut onto the receptacle will compress the split ring, causing the split ring to deform inwardly against the leg of the walking aid to retain the tip of the leg within the receptacle.

5. The electronic device of claim 1 wherein a duration of the rehabilitation period is longer than one day, wherein the at least one time interval of the rehabilitation period is a plurality of time intervals collectively spanning the rehabilitation period, and wherein the identifying of the currently operative time interval of the rehabilitation period comprises:
    determining a current date; and
    choosing one of the plurality of time intervals that includes the current date as the currently operative time interval.

6. The electronic device of claim 1 wherein the target load on the walking aid during the time interval is a target absolute load on the walking aid during the time interval and further comprising:
    a user input mechanism, communicatively coupled to the processor, for receiving user input specifying:
        a patient weight;

a target relative load on an injured lower extremity during the time interval, the target relative load being relative to the patient weight; and a duration of the time interval during which the target relative load on the injured lower extremity is to be operative, and wherein the processor is operable to compute the target absolute load on the walking aid based on the patient weight and the target relative load on the injured lower extremity during the time interval.

7. The electronic device of claim 6 wherein the processor is further operable to, upon expiry of the time interval during which the target relative load on the injured lower extremity is to be operative, provide a user indication indicating that the target relative load on the injured lower extremity is no longer in effect.

8. The electronic device of claim 7 wherein the user indication comprises a prompt for entry of further user input, via the user input mechanism, specifying:

a new target relative load on the injured lower extremity; and a new time interval of the rehabilitation period during which the new target load on the walking aid is to be operative.

9. The electronic device of claim 1 wherein the processor is further operable to store, in the memory, historical usage data comprising, for each of a plurality of previously taken patient steps, an indication of the determined peak load on the walking aid during the patient step.

10. A system for promoting proper use of a walking aid during patient rehabilitation from a lower extremity injury, the system comprising:

an electronic device associated with the walking aid, the electronic device comprising:

a body having a receptacle configured to receive a tip of a leg of the walking aid;

a substantially cylindrical housing configured to cooperate with the body to define an enclosed annular space;

at least one load sensor anchored to the body, the at least one load sensor being configured to measure a load on the walking aid;

a processor housed within the enclosed annular space, the processor communicatively coupled to the at least one load sensor;

a retaining mechanism for retaining the tip of the leg of the walking aid within the receptacle;

a base configured for limited axial movement relative to the body; and a foot at a lower end of the base, wherein the at least one load sensor is disposed between the base and the body and is configured to bear a load placed upon the walking aid during use of the walking aid;

a computing device comprising a processor and memory storing instructions that, when executed, cause the computing device to:

receive rehabilitation program parameter data originating from a medical professional, the rehabilitation program parameter data including, for each of a plurality of time intervals spanning a rehabilitation period, a target relative load for an injured lower extremity during the time interval, the target relative load being relative to a patient body weight;

receive an indication of the patient body weight;

based on the rehabilitation program parameter data and the patient body weight, calculate, for each of the plurality of time intervals spanning the rehabilitation period, a target absolute load for the walking aid during the time interval; and output rehabilitation program data comprising a schedule for use by the electronic device associated with the walking aid, the schedule specifying:

the plurality of time intervals spanning the rehabilitation period; and for each of the plurality of time intervals spanning the rehabilitation period, a target absolute load for the walking aid during the time interval, wherein the processor of the electronic device is operable to automatically adjust, according to the schedule, a currently operative target absolute load on the walking aid by, periodically during the rehabilitation period:

based on a current date, identifying one of the time intervals of the schedule as currently operative;

using the at least one load sensor, determining a peak load on the walking aid during a patient step taken during the currently operative time interval; and providing a user notification indicating that the peak load upon the walking aid during the patient step is non-compliant with the target absolute load on the walking aid during the currently operative time interval.

11. The system of claim 10 wherein the walking aid is a pair of crutches or canes, wherein the electronic device is a first electronic device associated with a first crutch or cane of the pair, wherein the data from the at least one load sensor includes data indicative of a dynamic load on the first crutch or cane during the patient step, and wherein the electronic device further comprises:

a wireless transceiver configured to receive, from a second electronic device associated with a second crutch or cane of the pair, wireless signals carrying data indicative of a dynamic load on the second crutch or cane during the patient step; and wherein the determining of the peak load upon the walking aid during the patient step comprises:

generating, based on the data indicative of the dynamic load on the first crutch or cane and the data indicative of the dynamic load on the second crutch or cane, a representation of a dynamic load on the pair of crutches or canes collectively during the patient step; and based on the generated representation, determining a maximum load on the pair of crutches or canes during the patient step, wherein the peak load upon the walking aid during the patient step is the maximum load on the pair of crutches or canes during the patient step.

12. The system of claim 10 wherein the computing device is a mobile device, wherein the electronic device associated with the walking aid further comprises a wireless transceiver, and wherein the processor of the electronic device associated with the walking aid is further operable to cause wireless transmission, to the mobile device, for each of a plurality of patient steps taken during the rehabilitation period, of an indication of the determined peak load on the walking aid during the patient step.

13. The system of claim 12 wherein the mobile device comprises a display and wherein the processor of the mobile device is further operable to:

store, in the memory of the mobile device, historical usage data of the walking aid during the rehabilitation period, the historical usage data including the indications of the determined peak load on the walking aid during each of the plurality of patient steps taken during the rehabilitation period;

generate, based at least in part on the historical usage data, analytics indicative of the historical usage data of the walking aid during the rehabilitation period; and display, on the display of the mobile device, the generated analytics indicative of the historical usage data of the walking aid during the rehabilitation period.

14. The system of claim 13 wherein the displayed analytics indicative of the historical usage data of the walking aid during the rehabilitation period include a graphical indicator, for a chosen time interval of the rehabilitation period, indicating a proportion of patient steps taken during the chosen time interval that were compliant with the target absolute load for the walking aid during the chosen time interval.

15. The system of claim 14 wherein the proportion of patient steps is a first proportion of patient steps, the graphical indicator is a first graphical indicator, and wherein the displayed analytics further include:

a second graphical indicator indicating a second proportion of patient steps taken during the chosen time interval that were non-compliant with the target absolute load on the walking aid during the chosen time interval by virtue of insufficient load on the injured lower extremity; and a third graphical indicator indicating a third proportion of patient steps taken during the chosen time interval that were non-compliant with the target absolute load on the walking aid during the chosen time interval by virtue of excessive load on the injured lower extremity.

16. The system of claim 10 wherein the receptacle is threaded and wherein the retaining mechanism comprises:

a threaded nut; and a split ring made from a resilient material, the nut and the split ring being configured so that, when the tip of the leg of the walking aid is passed through both of the nut and the split ring and is received within the receptacle, threading of the nut onto the receptacle will compress the split ring, causing the split ring to deform inwardly against the leg of the walking aid to retain the tip of the leg within the receptacle.

* * * * *